United States Patent
Sinderbrand et al.

(10) Patent No.: US 9,202,066 B2
(45) Date of Patent: Dec. 1, 2015

(54) INTEGRATED HEALTH CARE SYSTEMS AND METHODS

(71) Applicant: Betterpath, Inc., Margate, NJ (US)

(72) Inventors: Gary Mark Sinderbrand, Linwood, NJ (US); Maxwell Shron, Brooklyn, NY (US); William Tate Cantrell, Jr., Falls Church, VA (US)

(73) Assignee: BETTERPATH, INC., Margate, NJ (US)

( * ) Notice: Subject to any disclaimer, the term of this patent is extended or adjusted under 35 U.S.C. 154(b) by 120 days.

(21) Appl. No.: 13/708,427

(22) Filed: Dec. 7, 2012

(65) Prior Publication Data

US 2014/0164784 A1    Jun. 12, 2014

(51) Int. Cl.
*G06F 21/60* (2013.01)
*G06Q 50/22* (2012.01)
*G06Q 50/24* (2012.01)
*G06F 19/00* (2011.01)
*H04L 29/06* (2006.01)

(52) U.S. Cl.
CPC ............ *G06F 21/602* (2013.01); *G06F 19/345* (2013.01); *G06F 19/3443* (2013.01); *G06Q 50/22* (2013.01); *G06Q 50/24* (2013.01); *G06F 19/322* (2013.01); *G06F 2221/2107* (2013.01); *H04L 63/0428* (2013.01)

(58) Field of Classification Search
CPC ....... G06F 21/10; G06F 21/72; G06F 21/602; G06F 2221/2107; G06F 19/345; G06F 19/322; G06F 19/3443; H04L 9/08; H04L 63/0428; G06Q 50/22; G06Q 50/24
USPC ......................................................... 713/189
See application file for complete search history.

(56) References Cited

U.S. PATENT DOCUMENTS

| | | | |
|---|---|---|---|
| 6,581,038 B1 | 6/2003 | Mahran | |
| 2003/0101076 A1 | 5/2003 | Zaleski | |
| 2005/0268094 A1* | 12/2005 | Kohan et al. | 713/165 |

(Continued)

FOREIGN PATENT DOCUMENTS

| | | |
|---|---|---|
| JP | 2002-056104 | 2/2002 |
| KR | 10-2012-0031223 | 3/2012 |

OTHER PUBLICATIONS

Kyung, Minjung; Gill, Jeff; Ghosh, Malay; Casella, George; "Penalized Regression, Standard Errors, and Bayesian Lassos", 2010, International Society for Bayesian Analysis, pp. 2-3.*

(Continued)

*Primary Examiner* — Michael Pyzocha
*Assistant Examiner* — Gregory M Elmore
(74) *Attorney, Agent, or Firm* — DLA Piper LLP (US)

(57) ABSTRACT

Systems and methods described herein may store and analyze patient data sets. A processor in communication with a database may generate a plurality of patient data sets, each of the patient data sets being associated with one of a plurality of patients and comprising an attribute. The processor may de-identify each of the patient data sets so that they are not associated with the patients. The processor may encrypt each of the de-identified data sets to generate a plurality of encrypted data sets and store the encrypted data sets in the database. The processor may analyze one of the patient data sets to determine a relationship between the one of the patient data sets and the other of the patient data sets based on the attribute of the one of the patient data sets and the attributes of the other of the patient data sets.

32 Claims, 22 Drawing Sheets

(56) References Cited

U.S. PATENT DOCUMENTS

| | | | |
|---|---|---|---|
| 2006/0080139 A1 | 4/2006 | Mainzer | |
| 2006/0155572 A1 | 7/2006 | Postrel | |
| 2007/0271121 A1 | 11/2007 | Laudan et al. | |
| 2008/0085272 A1 | 4/2008 | Kaplan | |
| 2008/0126134 A1 | 5/2008 | Jones et al. | |
| 2008/0172251 A1* | 7/2008 | Reichert et al. | 705/2 |
| 2008/0221923 A1 | 9/2008 | Shogan | |
| 2008/0222029 A1 | 9/2008 | Poster | |
| 2008/0294459 A1* | 11/2008 | Angell et al. | 705/2 |
| 2009/0299760 A1 | 12/2009 | Spradlin | |
| 2010/0015156 A1 | 1/2010 | Dubinsky et al. | |
| 2010/0125462 A1 | 5/2010 | Aggarwal | |
| 2010/0190162 A1 | 7/2010 | Rotter et al. | |
| 2010/0324936 A1 | 12/2010 | Vishnubhatla et al. | |
| 2011/0046979 A1 | 2/2011 | Tulipano et al. | |
| 2011/0071907 A1 | 3/2011 | Lewis | |
| 2011/0099140 A1 | 4/2011 | Ridgeway | |
| 2011/0166883 A1 | 7/2011 | Palmer et al. | |
| 2011/0229471 A1 | 9/2011 | Rotter et al. | |
| 2012/0073585 A1 | 3/2012 | Rotter et al. | |
| 2012/0190698 A1 | 7/2012 | Dubinsky et al. | |
| 2012/0208900 A1 | 8/2012 | Dubinsky et al. | |
| 2014/0257047 A1* | 9/2014 | Sillay et al. | 600/301 |

OTHER PUBLICATIONS

Kyung, M et al., "Penalized Regression, Standard Errors, and Bayesian Lassos", 2010, International Society for Bayesian Analysis, 5, No. 2, pp. 369-412.*

C.A. Siegal, L.S. Siegal, J.S. Hyams, S. Kugathasan, J. Markowitz, J.R. Rosh, N. Leleiko, D.R. Mack, W. Crandall, J. Evans, D.J. Keljo, A.R. Otley, M. Oliva-Hemker, S. Garrior, C.R. Langton, I.T. Wrobel, G. Wahbeh, J.A. Quiros, G. Silber, R.J. Bahar, B.E. Sands, and M.C. Bubinsky. *A Real-Time Tool to Display the Predicted Disease Course and Treatment Response for Children with Crohn's Disease*. Inflammatory Bowel Disease, vol. 17, Issue 1, pp. 30-38. Jan. 2011.

Gericke, C. A., "Ethical issues in funding orphan drug research and development," 2005, J. Med. Ethics; 21: 164-168.

International Search Report issued in PCT/US2012/068522 dated Aug. 22, 2013.

Written Opinion of the International Searching Authority issued in PCT/US2012/068522 dated Aug. 22, 2013.

English Language Abstract and Translation of JP 2002-056104 published on Feb. 20, 2002.

Related U.S. Appl. No. 13/313,863.

Foundation Center, "Guide to Funding Research," Feb. 8, 2007.

Torrey, Trisha, "The Role of Medical Research in Healthcare Reform," Mar. 28, 2009, About.com.

R.P. Sarma, Clinical Methods: The History, Physical, and Laboratory Examinations, "Red Cell Indices," 1990, Butterworth Publishers, 3rd Edition, pp. 720-723.

U.S. Appl. No. 13/313,863.

International Preliminary Report on Patentability issued in PCT/US2012/068522 dated Jun. 9, 2015.

* cited by examiner

| Attribute | Value Range | Impact Weighted |
|---|---|---|
| Gender | M/F | No |
| Date of birth | Date | Yes |
| Date, age of onset | Date/# | Yes |
| Date, Age at diagnosis | Date/# | Yes |
| Current age | # | Yes |
| Anatomic involvement | Mild/Moderate/Severe M/M/S | Yes |
| Surgery of bowel Date(s), age and type | Date Age Type | Yes |
| Extra intestinal manifestations Date(s), age and type | Date Age Type | Yes |
| Interventions: Clinic visits | #, dates | Yes |
| Interventions: Endoscopy | #, dates | Yes |
| Interventions: Radiology | #, dates | Yes |
| Interventions: Lab Work | #, dates | Yes |
| Medication history -At onset -Currently -Ever on steroids? Complications from medications | Therapy Therapy Y/N How long/how many time Y/N | Yes |
| Hospitalization Timing preceding interventions Timing following intervention | Y/N #days #days | Yes |
| Total days of each hospitalization | # | Yes |

FIG. 3A

INTEGRATED HEALTH CARE SYSTEMS AND METHODS

BRIEF DESCRIPTION OF THE DRAWINGS

FIG. 3A depicts example input attributes according to an embodiment of the invention.

DETAILED DESCRIPTION OF SEVERAL EMBODIMENTS

Figure 1:
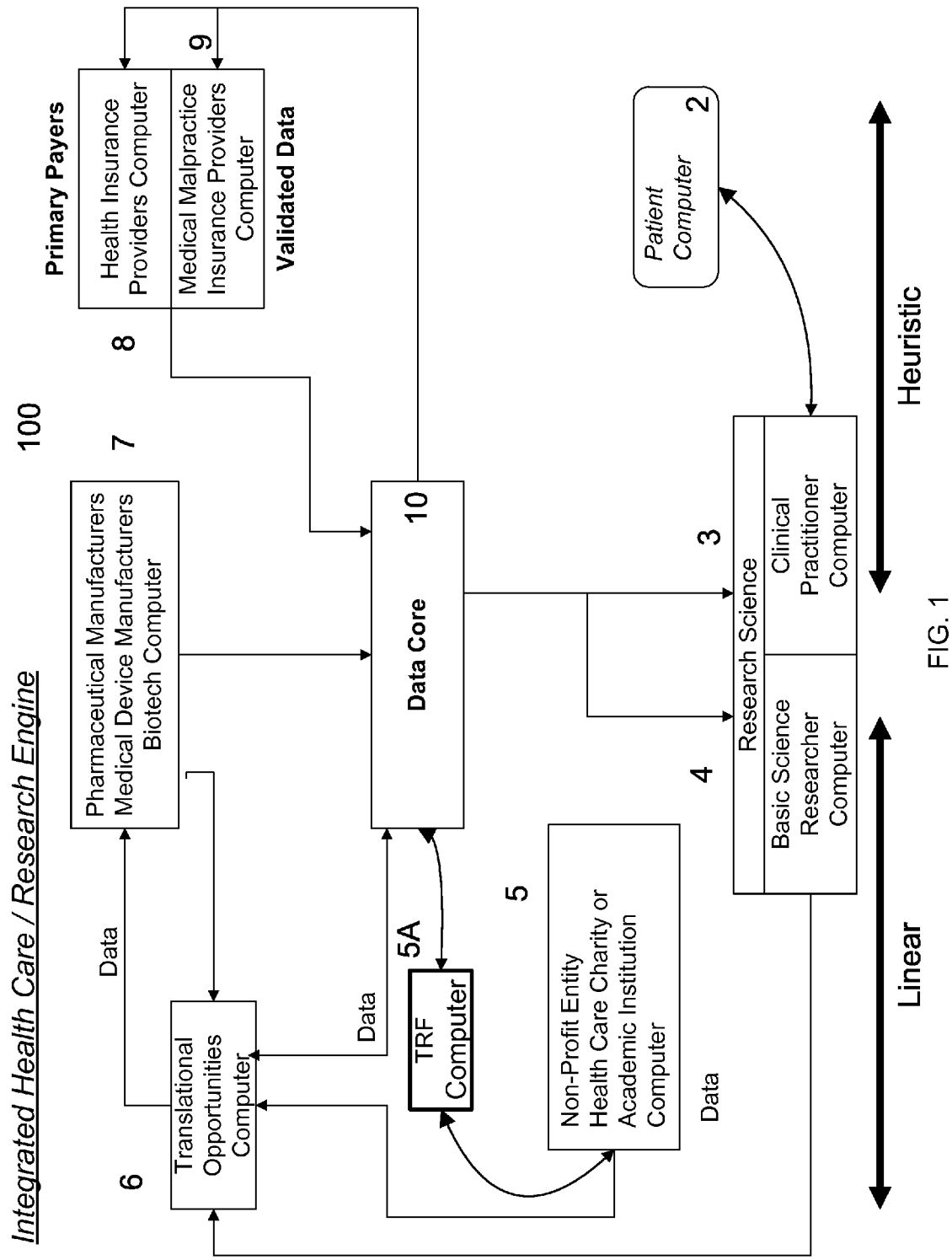
FIG. 1 depicts an integrated health care and research engine according to an embodiment of the invention.

Many diseases requiring long term clinical & therapeutic care may lack a consistent treatment approach based on the most relevant available data. Wide variation in treatment decisions across phenotypically similar cohorts may produce "anecdotal pockets" of optimized care (as measured by outcome), but these variations may be difficult to understand. However, a patient cohort may be characterized by a discrete set of attributes. By analyzing the evolution of an individual's disease course against the larger cohort, an understanding of why a particular individual did better or worse than a comparative sub cohort (the anecdotal pocket) may be obtained. As data about individuals and cohorts accumulates, a newly diagnosed patient may be aligned into a sub-cohort with an optimized outcome as measured by cost and quality of life.

Systems and methods described herein may forecast projected cost outcomes, which may allow patients and/or clinicians to consider a wider variety of treatment options while aligning payers with cost effective and/or non-complex paths chosen by patients and their health care professionals. Thus, optimized care as measured by complexity and cost to patients suffering from auto-immune/chronic illness may be provided. Data gathered and generated by the systems and methods described herein may be useful for other purposes as well, which will be explained in greater detail below.

Evidence based medicine may strongly encourage physicians to methodically proceed through identical treatment steps for each patient presenting with a similar diagnosis. An alternative to evidence based medicine is personalized medicine. Personalized medicine may favor immediate use of a projected effective treatment of an individualized symptomology, without prerequisite treatment steps that may lead to higher long term cost and disease complexity as disease activity persists and damage to the patient accumulates. Previously identified disease specific attributes may be securely input, stored, and expressed, and this data may be used to demonstrate that an individual patient in consultation with their clinician should deviate from the statistically more common therapeutic regime in some cases. Such personalized treatment may ultimately prove more efficient and more economical than common treatment because it may eliminate the employment of common therapeutic steps likely to be ineffective in the case of the individual patient when likelihood of ineffectiveness is identifiable through the patient's attributes. Personalized treatment may also reduce or eliminate the provision of healthcare to patients that requires them to undergo imprecisely targeted and/or potentially harmful therapies that may prolong or even exacerbate illnesses. The results of opting to undergo personalized treatment may include better patient outcomes, greater clarity for patients and healthcare providers regarding treatment choices, and/or cost savings for the payer of healthcare costs due to an increased likelihood of selecting an effective therapy early in the treatment process.

As will be described in greater detail below, patient data may be collected, organized, and analyzed in relation to current results of actual medical treatments. The data may then be compared to a larger sample of previously entered patient records. Some patients that suffer from certain conditions, such as auto-immune/chronic illnesses, may fall into expected cost outcome categories that do not match actual outcome (patient experience). These outliers may be identified, and the patient/clinician may be informed that there may be another treatment pathway available that may result in less complexity and cost over time. This may provide the physician and the patient with real-time views of likely courses of a patient's disease based on current treatment complexity as well as any projected treatment. Storage and calculation of individual disease attributes may be individualized to meet the needs of each end-user. Other end-users could include health insurance companies, pharmaceutical companies, self-insuring corporations, basic science researchers, and/or non-profit institutions, for example.

In the case of a health insurer, for example, the insurer may use the information to determine that clinical and/or basic science evidence demonstrates that the early use of a more expensive therapy for the treatment of a patient will reduce the overall cost of treatment of that patient over the course of the patient's life. This may be true even if the researched therapy is more expensive than other treatments, since its efficacy will eliminate the need for those other treatments and/or reduce the risk of complications or side effects that will lead to additional treatment and additional expenses. As a result, the insurer may approve payment for the initially more expensive therapy without requiring other "evidence-based" therapeutic practices to be exhausted first. This may cause the patient and clinician to modify the direction of treatment because a more effective treatment is evidenced and can be executed at lower total cost. This may also result in lower costs to the health insurer or employer in the case of self-insured corporations.

Secure, multi user systems and methods described herein may comprise one or more computers. A computer may be any programmable machine capable of performing arithmetic and/or logical operations. In some embodiments, computers may comprise processors, memories, data storage devices, and/or other commonly known or novel components. These components may be connected physically or through network or wireless links. Computers may also comprise software which may direct the operations of the aforementioned components. Computers may be referred to with terms that are commonly used by those of ordinary skill in the relevant arts, such as servers, PCs, mobile devices, and other terms. Computers may facilitate communications between users, may provide databases, may perform analysis and/or transformation of data, and/or perforin other functions. It will be understood by those of ordinary skill that those terms used herein are interchangeable, and any computer capable of performing the described functions may be used. For example, though the term "server" may appear in the following specification, the disclosed embodiments are not limited to servers.

Computers may be linked to one another via a network or networks. A network may be any plurality of completely or partially interconnected computers wherein some or all of the computers are able to communicate with one another. It will be understood by those of ordinary skill that connections between computers may be wired in some cases (i.e. via Ethernet, coaxial, optical, or other wired connection) or may be wireless (i.e. via Wi-Fi, WiMax, or other wireless connection). Connections between computers may use any protocols, including connection oriented protocols such as TCP or connectionless protocols such as UDP. Any connection through which at least two computers may exchange data can be the basis of a network.

FIG. 1 depicts an integrated health care and research engine 100 according to an embodiment of the invention. The engine 100 may include a computer or network of multiple computers. The engine 100 may include a data core 10, which may include one or more databases associated with one or more computers which may receive, compile, and/or analyze data from one or more sources. The data core 10 may include one or more secure databases, but data within the data core 10 may be accessible by various parties and/or computers for various purposes. For example, computers associated with patients 2, clinical practitioner computers 3, basic science researcher computers 4, non-profit entity computers 5 such as computers associated with health care charities or academic institutions (and/or targeted research funding providers 5A working with such entities), translational opportunity identifier computers 6 such as computers associated with system administrators, manufacturer computers 7 such as computers associated with pharmaceutical or medical device manufacturers and biotech companies, health insurance provider computers 8, and/or medical malpractice insurance provider computers 9 may be able to access and/or contribute to the data in the data core 10. Furthermore, information may be delivered to the providers in some cases. For example, a translational opportunity identifier computer 6 may automatically generate and send an email or other communication to a researcher computer 4 if it identifies an opportunity for research that matches a researcher's interests and/or background. In another example, a patient computer 2 may be automatically informed of a study which matches a condition or disease of the patient and may present an opportunity to participate to the patient. Reference to FIG. 1 will be made in greater detail below as the relationships of these various computers to the data core 10 are explained.

In FIG. 1, computers on the left side of the engine diagram (basic science researcher computers 4, non-profit entity computers 5, translational opportunity identifier computers 6, and manufacturer computers 7) are labeled as "linear" and computers on the right side of the diagram (patient computers 2, clinical practitioner computers 3, health insurance provider computers 8, and medical malpractice insurance provider computers 9) are labeled as "heuristic." Linear processing may involve sorting the data in the data core 10 to find a singular outcome; i.e. in the case of a pharmaceutical company looking to identify patients with blue eyes between the ages of 16 and 27 who live in the Midwest. For example, a data sort function may be run to produce a list of names that match. In another example a researcher computer 4 could request all patients that currently take drug X and drug Y in order to do a comparative effectiveness study. A researcher may believe that a certain genetic mutation may respond to an "orphan drug" and wish to scan the data core for patients with that trait. In the case of targeted research funding (TRF), the research non profit or academic institution computer 5 may be focused on translational projects which may require the participation of certain subsets of patients that fit a specific attribute profile. No advanced modeling or "what if" (heuristic) calculations may be needed to find such subjects.

Heuristic processing may employ non-deterministic algorithms to simulate a variety of outcomes by inputting different variables, for example to optimize a patient's cost and complexity outcome. Computers on the heuristic side may each have specific GUIs that may target areas of specific concern or interest. Heuristic processing may involve experience-based techniques for problem solving, learning, and discovery. For example, where an exhaustive search is impractical, heuristic methods may be used to speed up the process of finding a satisfactory solution.

Figure 2:
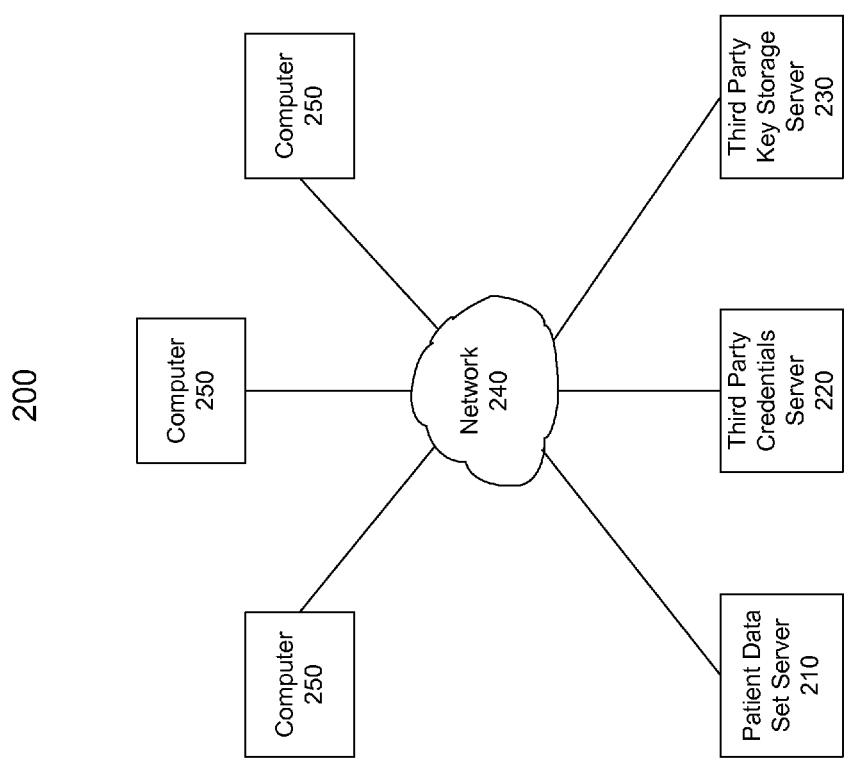
FIG. 2 depicts a computer network according to an embodiment of the invention.

FIG. 2 depicts a computer network 200 according to an embodiment of the invention. The network 200 may include one or more servers such as a patient data set server 210, a third party credentials server 220, and/or a third party key storage server 230, each of which may be in communication with one another via a public or private network 240 such as the Internet or via other means. Some or all of the servers, for example the patient data set server 210, may house and/or manage the data core 10. The various servers may be elements of a single sub-network or they may be organized separately. For example, a third party credentials server 220 and/or a third party key storage server 230 may be managed by third party security services providers separate from the patient data set server 210. Other computers 250 may communicate with some or all of the servers via the network 240 or other means. For example, computers 250 may be patient computers 2, clinical practitioner computers 3 or researcher computers 4, non-profit entity computers 5 or targeted research funding provider computers 5A, translational, opportunity identifier computers 6, manufacturer computers 7, and/or insurance provider computers 8/9. These computers 250 may send data to and/or receive data from the data core 10.

Patients and/or clinicians may enter data into the data core 10 through a user interface associated with a computer 250. The user interface may be designed to capture a series of facts about the individual's diagnosis, course of treatment(s), environmental and social information, and/or other data. Clinical outcomes may initially be entered retrospectively and then may be updated as needed. Some attributes may be disease specific attributes. For example, phenotypic and/or physician records, genetic records, family histories, and/or medications being taken may be entered into the data core 10. Additionally, patients may enter data at an initial event such as a first diagnosis and ongoing at regular intervals. For example, a complete update may be done during a clinical visit. Questions for a patient at a clinical visit may focus on environmental issues as well as general patient perception of their own health. The system may monitor for unusual changes in daily activity level, diet, other illnesses, and/or other medications introduced since the last update, for example.

FIG. 3A provides an example of several attributes which may be entered into the data core 10. These input variables or attributes may grow over time to include supplemental information that captures comprehensive environmental and genetic data. As new records are added to the data core 10, the system may become smarter over time through the accumulation of more data.

Figure 3B:
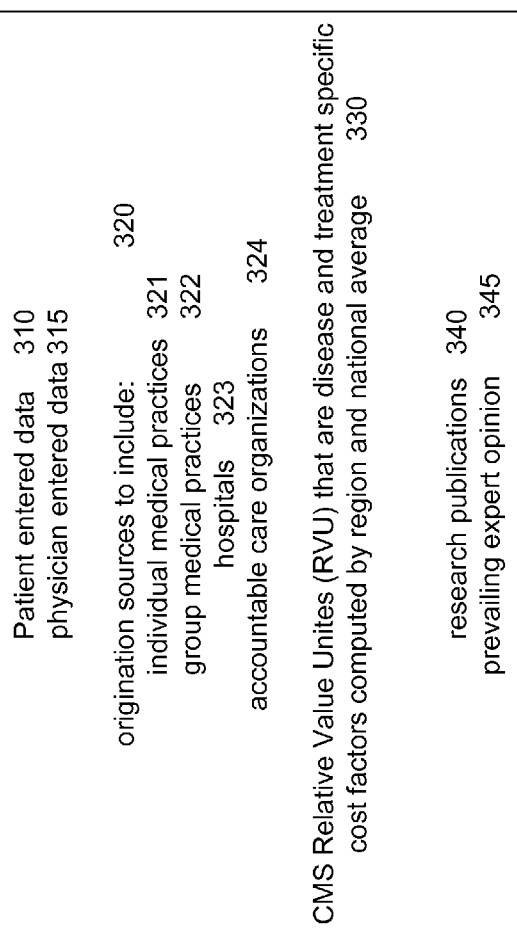
FIG. 3B depicts a plurality of input sources according to an embodiment of the invention.

FIG. 3B depicts a plurality of input sources 300 according to an embodiment of the invention. These input sources 300 may provide data for the data core 10. The input sources 300 may be associated with computers 250 associated with patients 2, clinical practitioners 3 or researchers 4, non-profit entities 5 or targeted research funding providers 5A, translational opportunity identifiers 6, manufacturers 7, and/or insurance providers 8/9. For example, patient entered data 310 and/or physician entered data 315 may be provided. This data 310/315 may include information such as that shown in FIG. 3A. Patient and/or physician entered data 310/315 may be associated with an origination source 320. Origination sources 320 may include individual medical practices 321, group medical practices 322, hospitals 323, accountable care organizations 324, or others, each of which may be associated with one or more computers 250. Input sources 300 may also include cost factors 330. These cost factors 330 could be, for example, Centers for Medicare and Medicaid Services (CMS) relative value units (RVUs) that may be disease and/or treatment specific, and may be computed according to regional and/or national averages for particular diseases and/or treatments. Research publications 340 and prevailing expert opinions 345 may also be input sources 300 for the data core 10.

Figure 4:
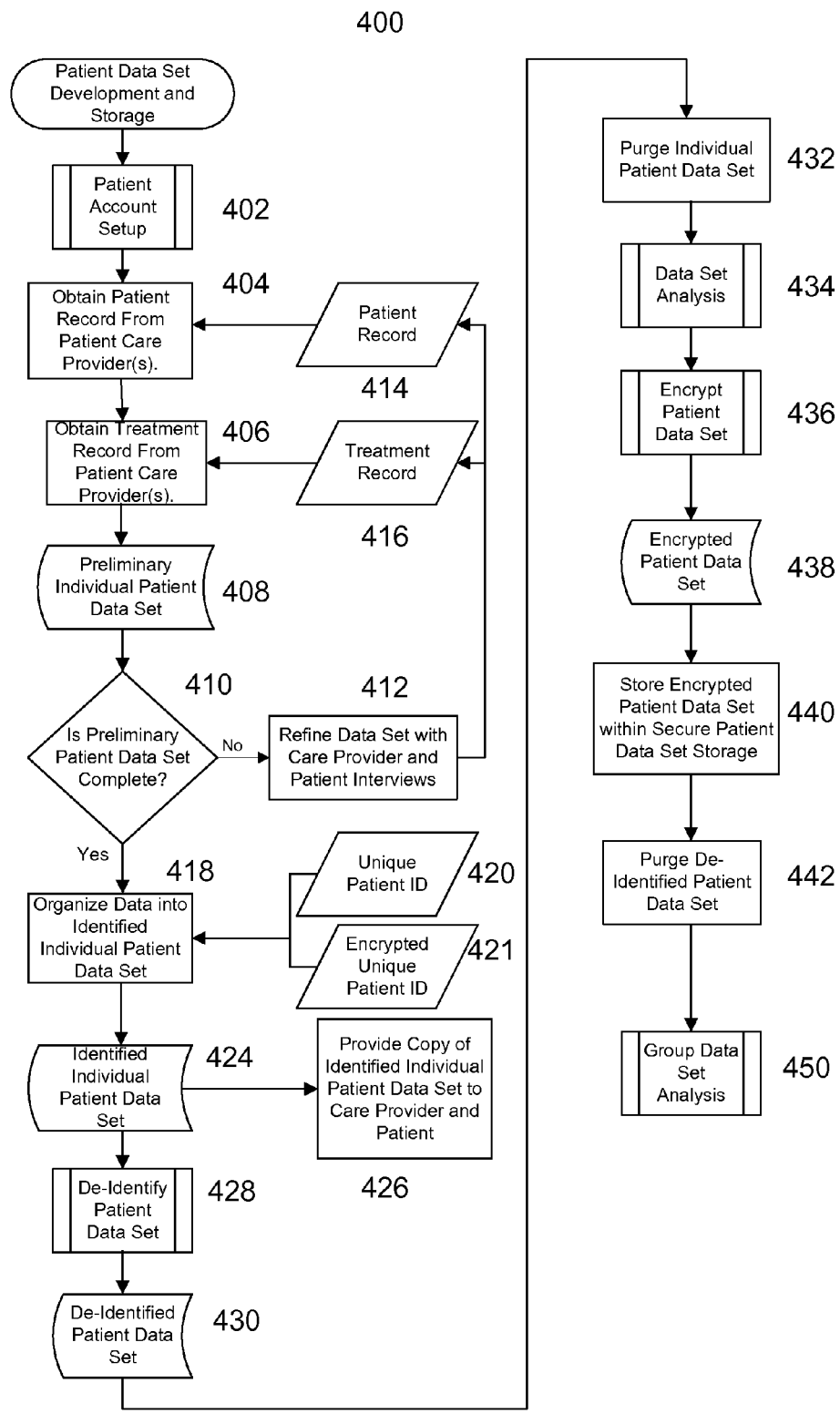
FIG. 4 depicts a patient data set development and storage process according to an embodiment of the invention.

FIG. 4 depicts a patient data set development and storage process 400 according to an embodiment of the invention. This process 400 may be performed by one or more computers 250. The process 400 may enable entry of patient data for a particular patient into the data core 10. First, a patient account may be set up 402, 500. An example of a patient account setup process 500 is described in greater detail with respect to FIG. 5 below. When the patient account has been created, one or more patient records 414 associated with the account may be obtained from the patient or a care provider 404. Patient treatment records 416 may also be obtained 406. A preliminary individual patient data set may be assembled 408 from the patient records 414 and/or patient treatment records 416 that are received. The preliminary data set may be analyzed for completeness 410. This analysis may include verifying that data attributes are present and determining that values associated with the attributes are within an expected or possible range. If the preliminary data set is incomplete, additional and/or corrected data may be obtained 412, for example through care provider and/or patient input or interviews. Corrected data may be added to the patient records 414 and/or patient treatment records 416, the preliminary data set may be rebuilt 408, and the preliminary data set may be analyzed again 410. If the preliminary data set is complete, the data therein may be organized into an identified individual patient data set 418. The identified individual data set may be a verified data set that may be ready for de-identification. The identified individual data set may be generated from a preliminary data set which is complete. A unique patient ID may be assigned to the set 420, and an encrypted unique patient ID may also be assigned to the set 422. Once these identifiers are assigned, the identified individual patient data set may be formed 424, and a copy of the identified individual patient data set may be provided to care providers and/or the patient 426.

The identified individual patient data set may be de-identified 428, 600 to remove data that links the medical information in the data set to the identity of the associated patient. An example process for de-identifying a data set is discussed below in the context of FIG. 6. A de-identified patient data set may be formed 430 and purged of identifying data 432. The remaining data, which may include medical data, treatment data, and the like, may be analyzed 434, 700. An example analysis process is discussed below in the context of FIG. 7. The remaining data may also be encrypted 436, 1100. An example encryption process is discussed below in the context of FIG. 11. When an encrypted data set is formed 438, it may be stored 440 within a secure patient data set storage database, which may be part of the data core 10. The de-identified patient data set may be purged from memory 442. The de-identified patient data set may be purged so that future access to the data may be provided through the encrypted data set. To provide access to the data, the system may first perform a decryption process, such as the example process discussed below in the context of FIG. 10. Thereafter, the patient data set may be ready for analysis 450, for example as discussed below with respect to FIG. 15.

Figure 5:
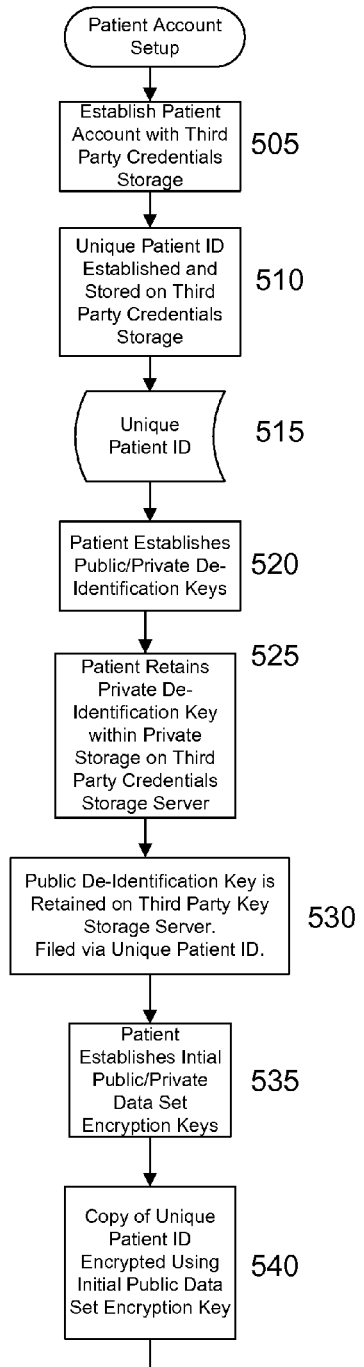
FIG. 5 depicts a patient account setup process according to an embodiment of the invention.
Figure 5:
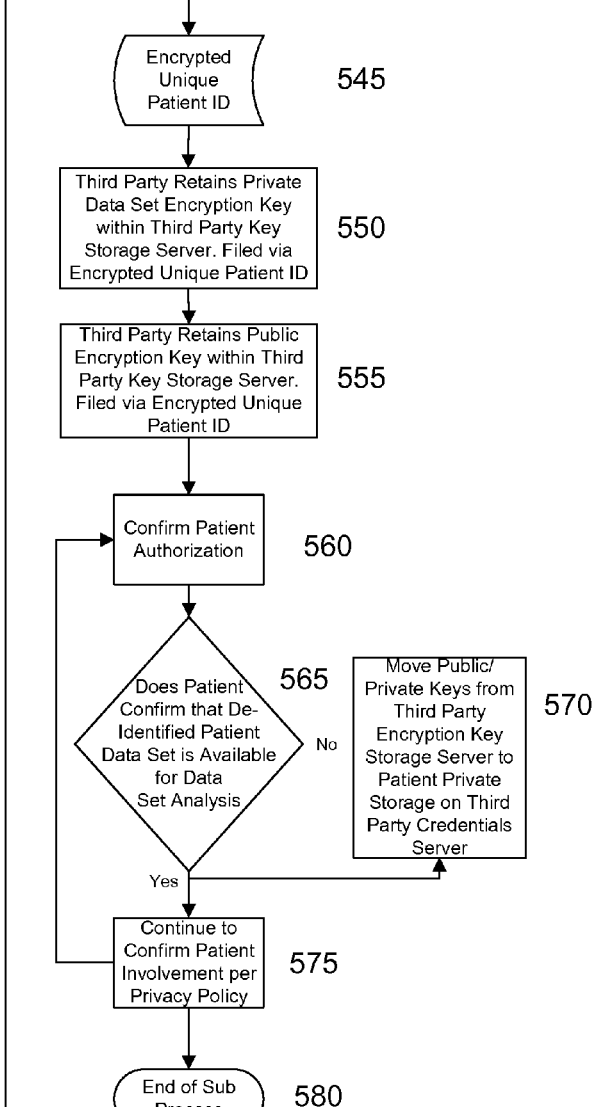

FIG. 5 depicts a patient account setup process 402, 500 according to an embodiment of the invention. This process 402, 500 may be performed by one or more computers, for example the patient data set server 210, third party credentials server 220, third party key storage server 230, other computer 250, or some combination thereof. Patient data held in the data core 10 may be de-identified and assigned a public-private key. The system may be a closed loop system in that the only way data may enter the data core 10 may be through following a set of specific steps such as that described above with respect to FIG. 4, and other external inputs may be forbidden. The closed loop system may be only accessible through specific permissions granted to each user. For example, the patient may have access to their personal health record within the engine at any time and may maintain the right to withdraw their data fully by withdrawing a key. The patient account setup process 402, 500, along with de-identification and encryption processes described below, may enable this security. A patient account may be established 505 with a third party credentials server 220, and a unique patient ID may be established and stored 510 on the third party credentials server 220. Once the patient ID is created 515, public and private de-identification keys for the patient may be established 520. The private de-identification key may be retained for the patient 525 on the third party credentials server 220. Optionally, the private de-identification key could be removed from the third party credentials server 220. This may be based on a patient preference selection received by the computer performing the setup process 402, 500. The public de-identification key may be retained on a third party key storage server 230 which may be separate from the third party credentials server 220 and filed on the third party key storage server 230 under a unique patient ID 530. When the de-identification keys have been established and stored, initial patient public and private data set encryption keys may be established 535. A copy of the unique patient ID may be encrypted using the initial public data set encryption key 540, producing an encrypted unique patient ID 545. The private data set encryption key may be stored within the third party key storage server 230 and filed with the encrypted unique patient ID 550. The public data set encryption key may also be stored within the third party key storage server 230 and filed with the encrypted unique patient ID 555. When the public and private data set keys have been established and stored, the system may confirm patient authorization for use of patient data 560. A check may be performed to confirm that the patient allows the de-identified patient data set to be made available for data set analysis 565. If the patient does not allow this access, public and private keys associated with the patient may be moved 570 from the third party encryption key storage server 230 to a patient private storage database on the third party credentials server 220 and the data may be disregarded in future data set analyses. If the patient allows the data set to be made available for data set analysis, the system may confirm patient involvement by presenting and receiving acceptance of a privacy policy 575. If the patient does not accept the policy, the system may retry to confirm patient authorization 560. If the patient accepts the policy, the patient account setup process 402, 500 may end, and the patient data set development and storage process 400 (or other process, if applicable) may proceed as described above.

Figure 6:
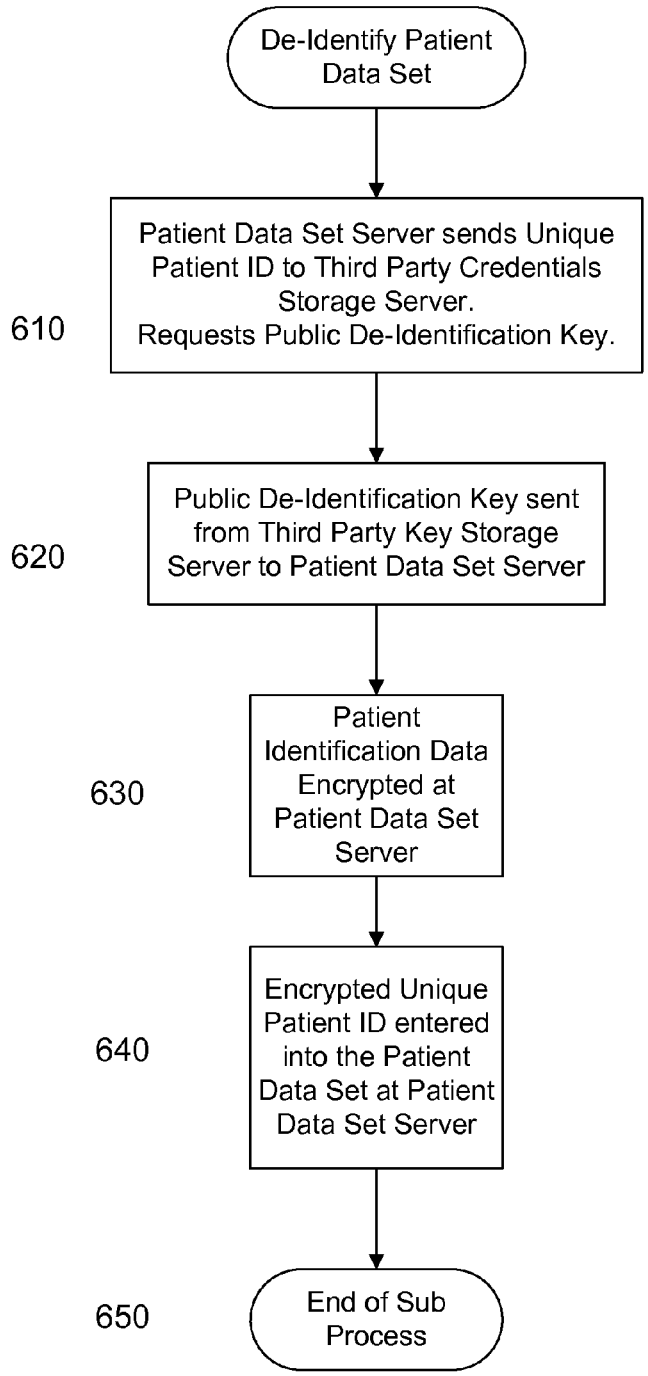
FIG. 6 depicts a de-identify patient data set process according to an embodiment of the invention.

FIG. 6 depicts a process 428, 600 which may generate a de-identified patient data set according to an embodiment of the invention. This process 428, 600 may be performed by one or more computers, for example the patient data set server 210, third party credentials server 220, third party key storage server 230, other computer 250, or some combination thereof. As discussed above, one or more computers may de-identify a patient data set before it is stored and made available in the data core 10. The de-identification process 428, 600 may disassociate the patient's identity data from data such as diagnosis, course of treatment(s), environmental and social information, and/or other data. A patient data set server 210 may send a unique patient ID to a third party credentials server 220 and request an associated public de-identification key 610. The third party key storage server 230, which may be in communication with the third party credentials server 220, may send this key to the patient data set server 210 in response 620. The patient data set server 210 may encrypt patient identification data 630 and enter the encrypted unique patient ID into the patient data set 640. After this is complete, the de-identify patient data set process 428, 600 may terminate 650, and the patient data set development and storage process 400 (or other process, if applicable) may proceed as described above.

Figure 7:
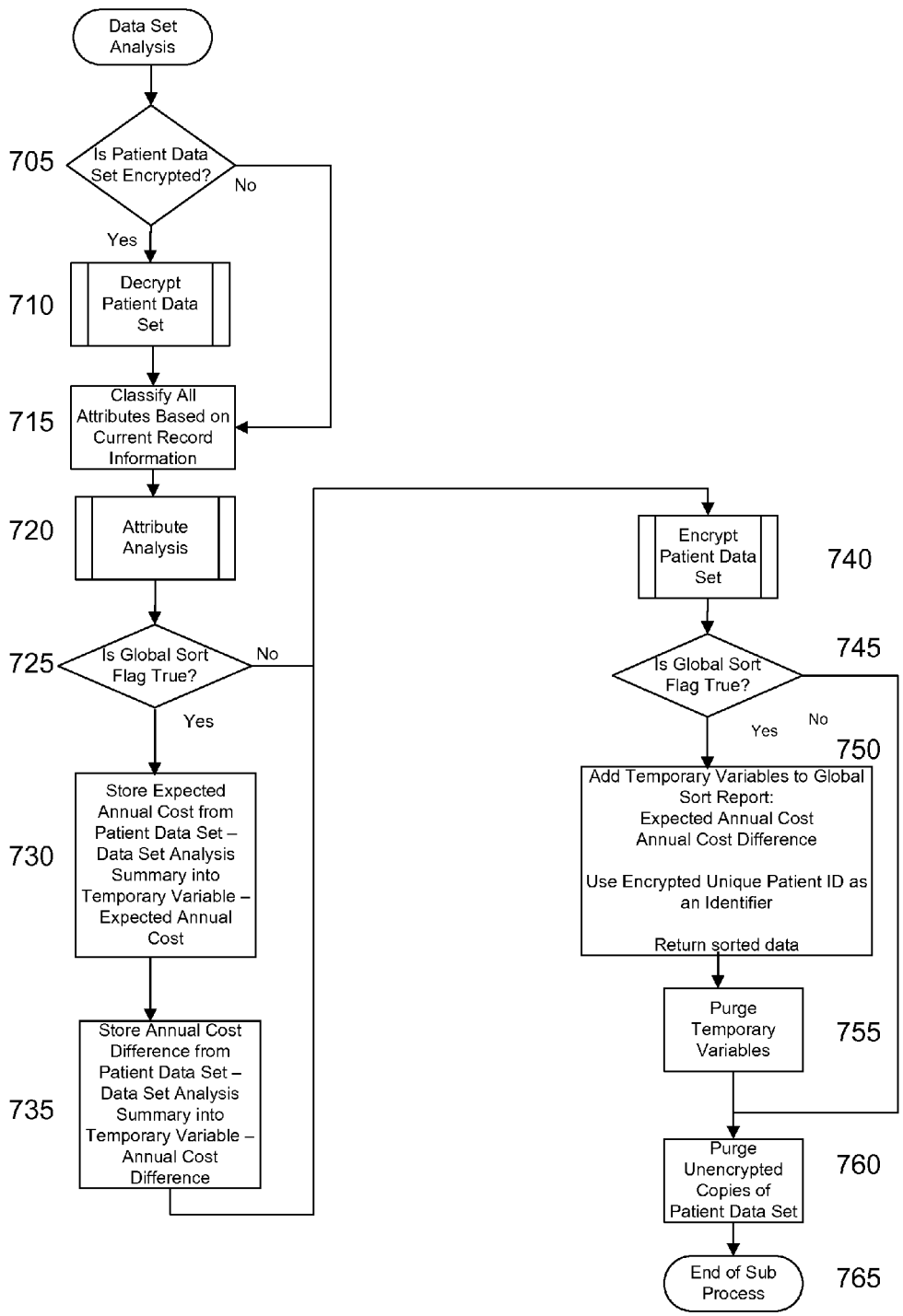
FIG. 7 depicts a data set analysis process according to an embodiment of the invention.

FIG. 7 depicts a data set analysis process 434, 700, 1225, 1530, 1630 for a particular patient according to an embodiment of the invention. This process 434, 700, 1225, 1530, 1630 may be performed by one or more computers, for example the patient data set server 210, third party credentials server 220, third party key storage server 230, other computer 250, or some combination thereof. Many types of information may be determined through data set analysis 434, 700, 1225, 1530, 1630. For example, the system may determine disease specific outcomes such as costs (which may include hard costs: days in hospital, cost of ongoing therapy and procedures; social costs: days missed from work/school; and/or costs solved for procedure code plus relative value units (RVU); for example) and/or complexities (which may include current projected disease path based on attributes; forecasted projected disease path based on user input; correlation analysis between current disease path and projected disease path based on attribution analysis; and/or forecast of cost and complexity based on heuristic inputs for example). An RVU may be a metric used to determine health care costs. For example, Medicare uses a physician fee schedule to determine payments for over 7,000 physician services. The fee for each service depends on its RVUs, which may rank on a common scale the resources used to provide each service. These resources may include the physician's work, the expenses of the physician's practice, and professional liability insurance. To determine the Medicare fee, a service's RVUs may be multiplied by a dollar conversion factor. Estimating and updating the RVUs may be a labor-intensive process because there are no readily available, up-to-date data on the resource requirements of each service.

First, the data set being analyzed may be checked for encryption 705. If the data set is encrypted, it may be decrypted 710, 1000. An example decryption process is presented below with respect to FIG. 10. If the data set was not encrypted, or after it has been decrypted 710, attributes within the data set may be classified based on current record information 715. Attributes may be classified and/or patients may be classified based on attributes in this process. The data core 10 may allow for a data sort by attribute(s) to find patients that have common characteristics. Once that group is identified, individual patients that fall into that sorted output may be examined, and each patient may be measured by actual cost and complexity. Individual outliers may be identified and then may be heuristically modeled for optimized outcomes. For example, if patient A has 11 of 20 attributes that indicate an outcome of moderate cost and complexity, and if a moderate cost and complexity outcome is the actual observed outcome, patient A may fall into the expected result group. If Patient B has only 5 of the 20 attributes, that person may fall outside patient A's grouping. If patient B's cost & complexity outcome (CCO) is aligned with patient A's CCO, but patient B's attributes indicate much less disease impact based on the grouping of patients with similar attributes, a clinician may use this information to model different approaches, Next, attribute analysis 720, 800 may be performed. An example attribute analysis process is presented below with respect to FIG. 8. After analysis, the system may check whether a global sort flag is set 725. If the global sort flag is set, an expected annual cost determined from the patient data set analysis may be stored into a temporary variable 730, and an annual cost difference between the expected annual cost and an average actual annual cost determined from the patient data set analysis may be stored into another temporary variable 735. After these values are stored, or if the global sort flag is not set, the patient data set may be encrypted 740, 1100. An example encryption process is presented below with respect to FIG. 11. If the global sort flag is set 745, the stored temporary variables may be added to a global sort report which may disclose data about the expected annual cost and/or annual cost difference 750. The global sort report may be a report generated using one or more of a variety of analytical processes. For example, a nearest neighbors analysis may be performed which may identify other data sets with which the patient data set shares attributes. The patient data set may be aligned with similar data sets, and nearest neighbors may be identified and distances from nearest neighbors in terms of similarity may be quantified. A cost sort may also be performed which may determine whether observed costs for the data set align with expected costs based on attributes. Actual and expected costs may be compared. The temporary variables may include additional information that can be modeled and/or added to the global sort report. For example, if actual and expected costs do not match for a patient data set, an alternative treatment may be modeled as a temporary variable and the alternative treatment costs may be compared to the actual and expected costs. The comparison results may be added to the global sort report. Since data is filed with the encrypted unique patient ID, the report may become non-useful once a record is de-encrypted again. This may allow the patient to be pulled out of the process at any time, even if old reports have their previous version of the encrypted unique patient ID. The temporary variables may then be purged from memory 755. If the global sort flag is not set, the process may skip dealing with the temporary variables 745, because no temporary variables were stored. Unencrypted copies of the patient data set may be purged from memory 760, and the data set analysis process 434, 700, 1225, 1530, 1630 may end 765. The patient data set development and storage process 400 (or other process, if applicable) may proceed as described above.

Figure 8:
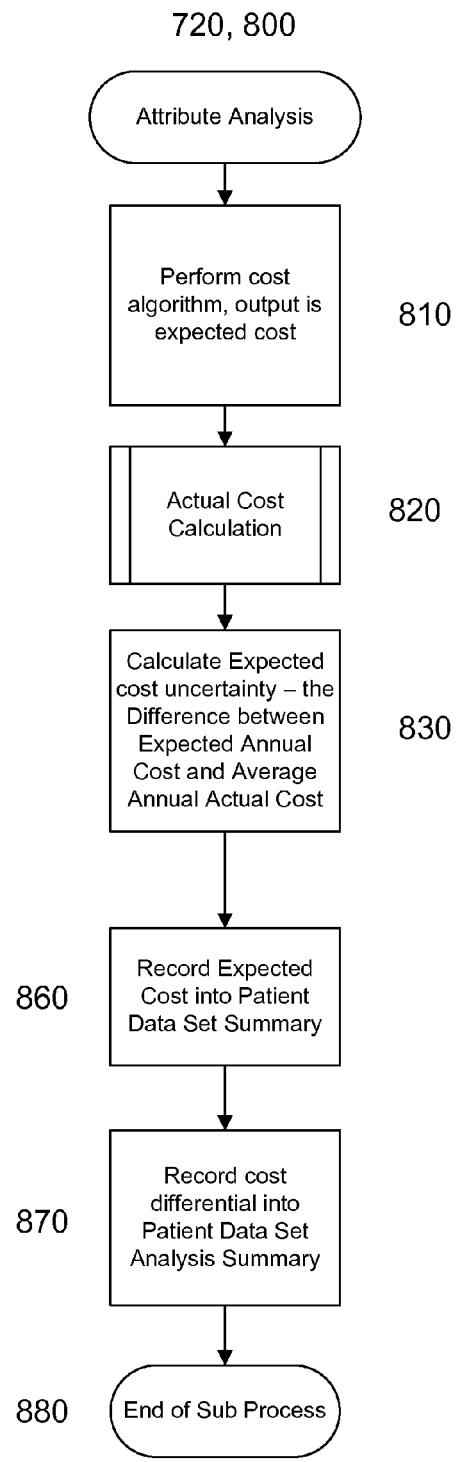
FIG. 8 depicts an attribute analysis process according to an embodiment of the invention.

FIG. 8 depicts an attribute analysis process 720, 800 according to an embodiment of the invention. This process 720, 800 may be performed by one or more computers, for example the patient data set server 210, third party credentials server 220, third party key storage server 230, other computer 250, or some combination thereof. An algorithmic analysis on attributes of a data set may be performed 810 and may output an expected cost value over a fixed time period as selected. Operations within the analysis process may fall into at least two categories: heuristic and linear. The heuristic, or "what if", data outputs may be customized for each user. For example, a patient computer 2 may display where the patient aligns relative to their attributes measured against all patients in the data core 10. The patient computer 2 may model an increasing number of actions that may project a likely CCO based on other patients' experiences. A patient computer 2 may be unable to display any identified data other than that of the associated patient. The patient computer 2 may also have access to personal patient data from any computer or like device. A clinician computer 3 may also display the patient's identified data as well as identified data for any other patients in the care of the associated clinician, but all other patients in the data core 10 may be de-identified. The clinician computer 3 GUI may forecast CCOs that can be expanded or restricted based on specific questions such as whether patients treated in the Northwest do better or worse than patients treated in the Midwest as measured by attribute alignment and CCOs. A penalized regression or classification model may be used in order to forecast expected cost and complexity outcomes. Linear operations may include researchers, basic science, nonprofit healthcare entities, academic institutions, as well as pharmaceutical manufactures, medical device manufacturers, and biotechnology firms. Next, an actual cost calculation may be performed 820, 900. An example actual cost calculation process is presented below with respect to FIG. 9. A cost difference between the expected cost and cost may be calculated 830. The expected cost may be recorded into the patient data set summary 860. The expected cost uncertainty or expected cost differential may also be recorded into the patient data set summary 870. For example, as described herein, a user such as a clinician may be able to examine the expected cost differential to determine whether cost differences warrant or justify a treatment change. After recording the expected cost 860 and uncertainty or differential 870, the process 720, 800 may terminate and the data set analysis process 434, 700 (or other process, if applicable) may proceed as described above.

Figure 9:
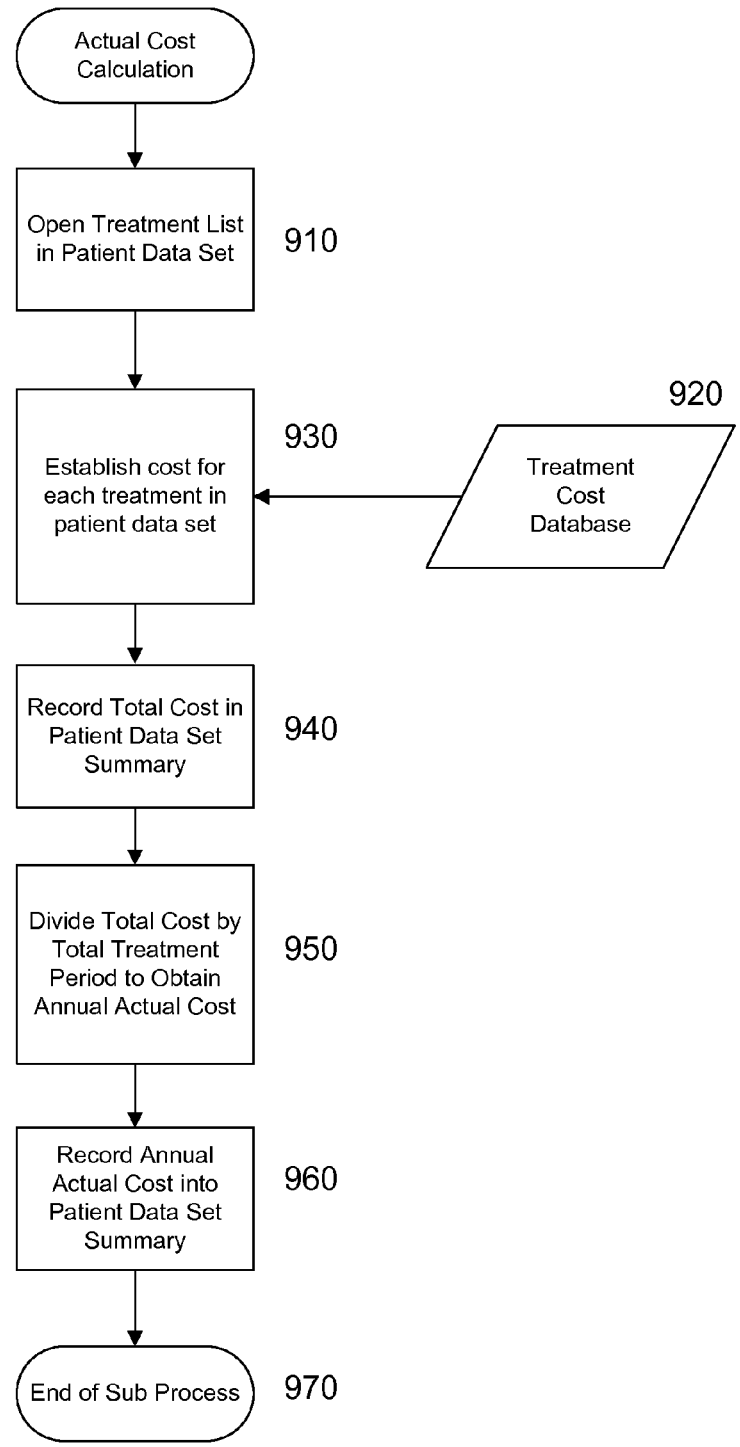
FIG. 9 depicts an actual cost calculation process according to an embodiment of the invention.

FIG. 9 depicts an actual cost calculation process 820, 900 according to an embodiment of the invention. This process 820, 900 may be performed by one or more computers, for example the patient data set server 210, third party credentials server 220, third party key storage server 230, other computer 250, or some combination thereof. The system may start by opening a treatment list in the patient data set 910 for a particular patient. For each treatment in the list, the cost for that treatment obtained from a treatment cost database 920 may be added to the total cost associated with the patient data set 930. The treatment cost database may be part of the data core 10 or may be some other database. The determined total cost may be recorded in the patient data set summary 940, and the total cost may be divided by a total treatment time period to obtain an annual actual cost 950. The actual annual cost may be recorded into the patient data set summary 960, and the process 820, 900 may terminate 970. Thereafter, the attribute analysis process 720, 800 (or other process, if applicable) may continue as described above.

Figure 10:
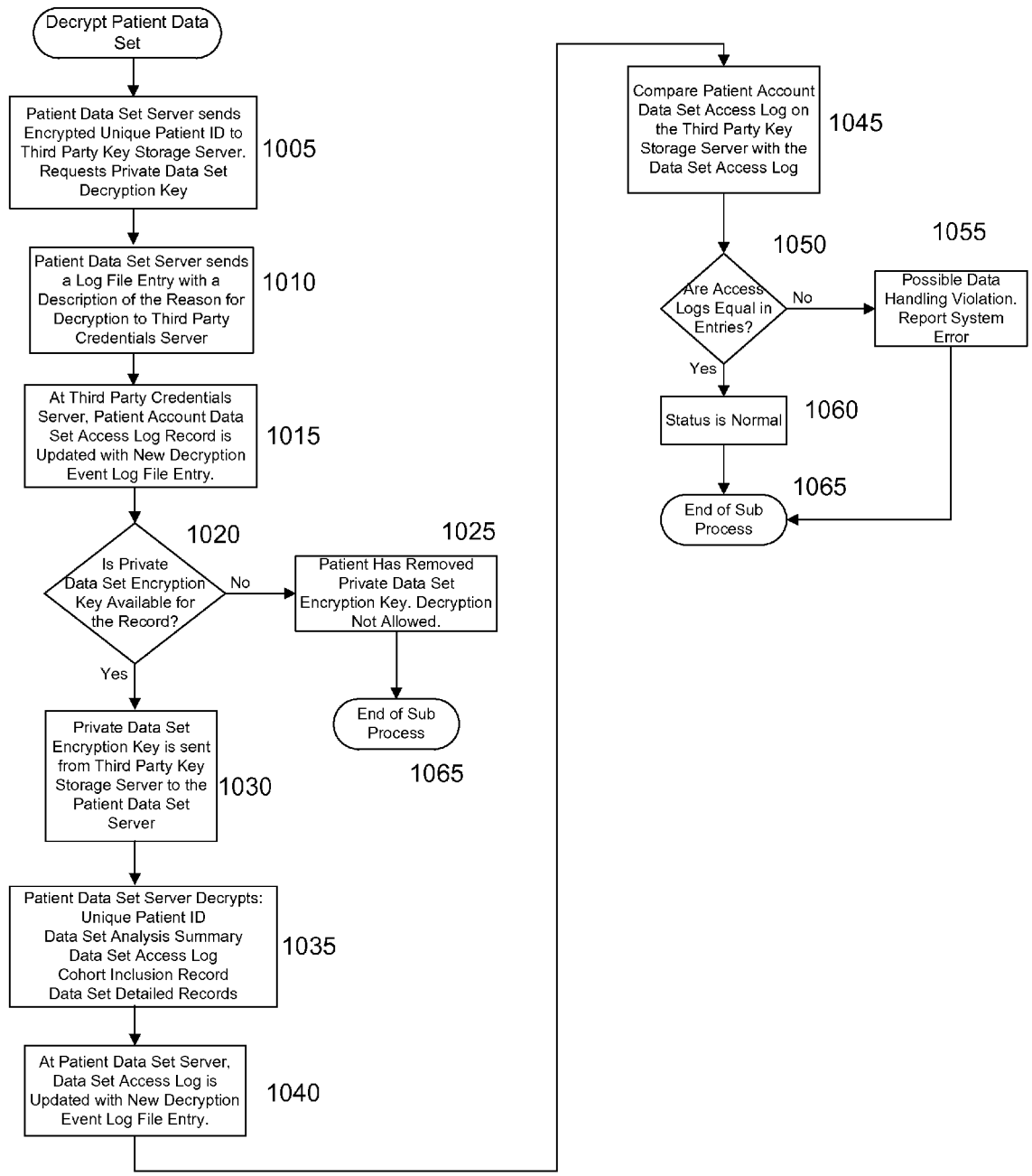
FIG. 10 depicts a patient data set decryption process according to an embodiment of the invention.

FIG. 10 depicts a patient data set decryption process 710, 1000, 1310, 1410 according to an embodiment of the invention. This process 710, 1000, 1310, 1410 may be performed by one or more computers, for example the patient data set server 210, third party credentials server 220, third party key storage server 230, other computer 250, or some combination thereof. A patient data set server 210 may send an encrypted unique patient ID to a third party key storage server 230 and request an associated private data set decryption key 1005. The patient data set server 210 may also send a log file entry with a description of a reason for decrypting the data set 1010 to a third party credentials server 220. The third party credentials server 220 may update a patient account data set access log with an entry of the new decryption event that has been initiated 1015. A check may be performed to determine whether a private data set encryption key is available for the patient record 1020. If no private data set encryption key is available, the system may determine that the patient has removed the associated private data set encryption key 1025. Therefore, decryption may be disallowed, the process 710, 1000, 1310, 1410 may be terminated 1065, and the data set analysis process 434, 700 (or other process, if applicable) may continue as described above.

If a private data set encryption key is available for the patient record, the private data set encryption key may be sent 1030 from the third party key storage server 230 to the patient data set server 210. The patient data set server 210 may decrypt data within the data set, thereby extracting information such as the unique patient ID, a data set analysis summary, a data set access log, a cohort inclusion record, and/or data set detailed records 1035. The patient data set server 210 may update the data set access log with a new decryption event log file entry 1040. The patient account data set access log on the third party key storage server 230 may be compared with the extracted and updated data set access log 1045. If the logs are determined to be different 1050, a possible data handling violation and/or system error may be reported 1055. If the logs match 1050, a normal status may be identified 1060. After reporting 1055 or determining normal status 1060, the process 1000 may be terminated 1065, and the data set analysis process 434, 700 (or other process, if applicable) may continue as described above.

Figure 11:
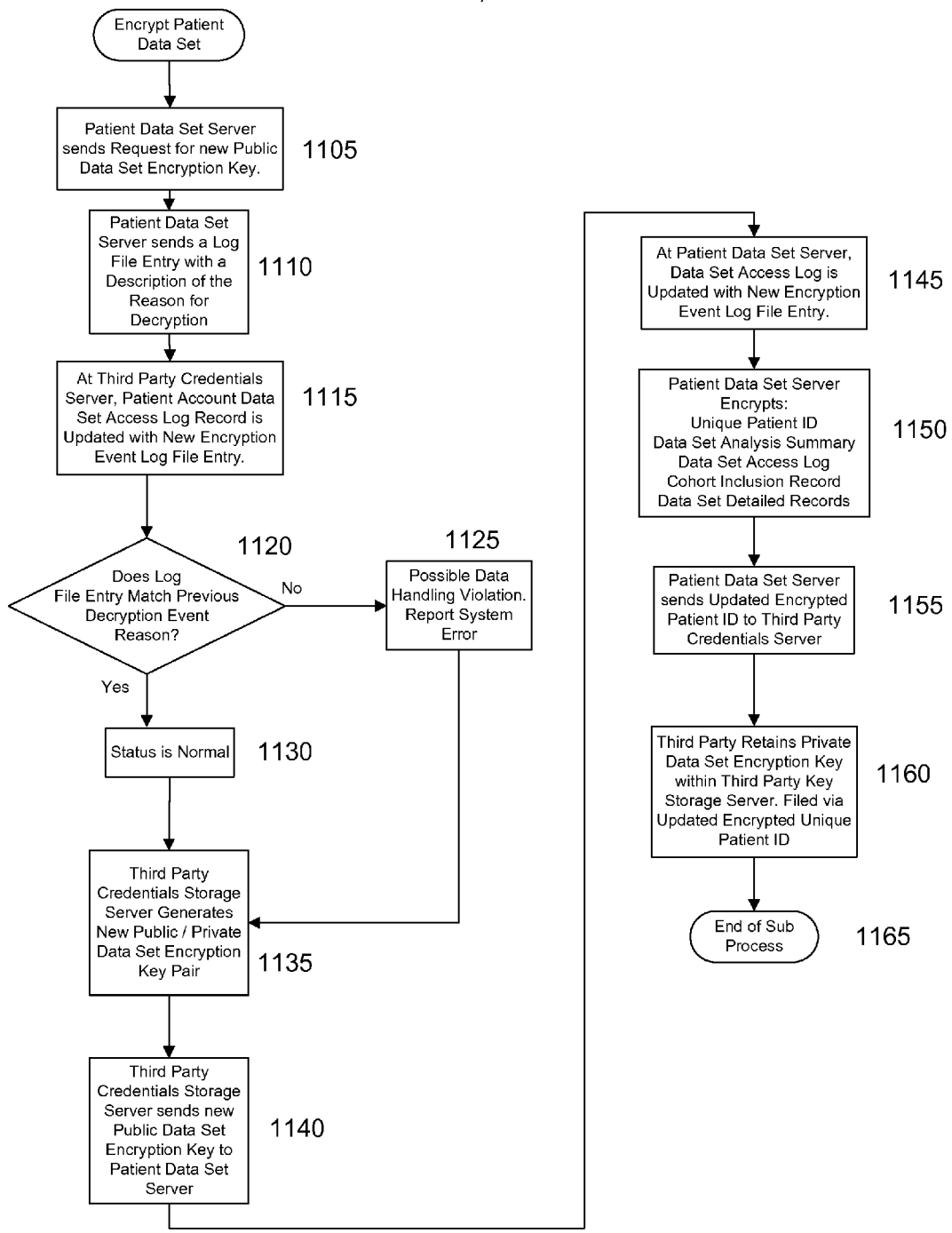
FIG. 11 depicts a patient data set encryption process according to an embodiment of the invention.

FIG. 11 depicts a patient data set encryption process 436, 740, 1100, 1340, 1450 according to an embodiment of the invention. This process 436, 740, 1100, 1340, 1450 may be performed by one or more computers, for example the patient data set server 210, third party credentials server 220, third party key storage server 230, other computer 250, or some combination thereof. The patient data set server 210 may send a request for a new public data set encryption key 1105. The patient data set server 210 may also send a log file entry to a log file on the third party credentials server 220 with a description of a reason for decryption 1110. The third party credentials server 220 may update the patient account data set access log record with a new encryption event log file entry 1115. A check may be performed to determine whether the log file entry matches a previous decryption event reason 1120. If no match is detected, a possible data handling violation and/or system error may be reported 1125. If a match is detected, a status may be determined to be normal 1130. In either case, the third party credentials server 220 may generate a new public and private data set encryption key pair 1135 and send the new public data set encryption key 1140 to the patient data set server 210. The patient data set server 210 may update the data set access log with a new encryption event log file entry 1145. The patient data set server 210 may also encrypt data within the data set, such as the unique patient ID, a data set analysis summary, a data set access log, a cohort inclusion record, and/or data set detailed records 1150. The patient data set server 210 may then send the updated encrypted patient ID 1155 to the third party: credentials server 220. The third party key storage server 230 may store the private data set encryption key and file it with the updated encrypted unique patient ID 1160. Then the process 436, 740, 1100, 1340, 1450 may end 1170, and the data set analysis process 434, 700 (or other process, if applicable) may continue as described above.

Figure 12:
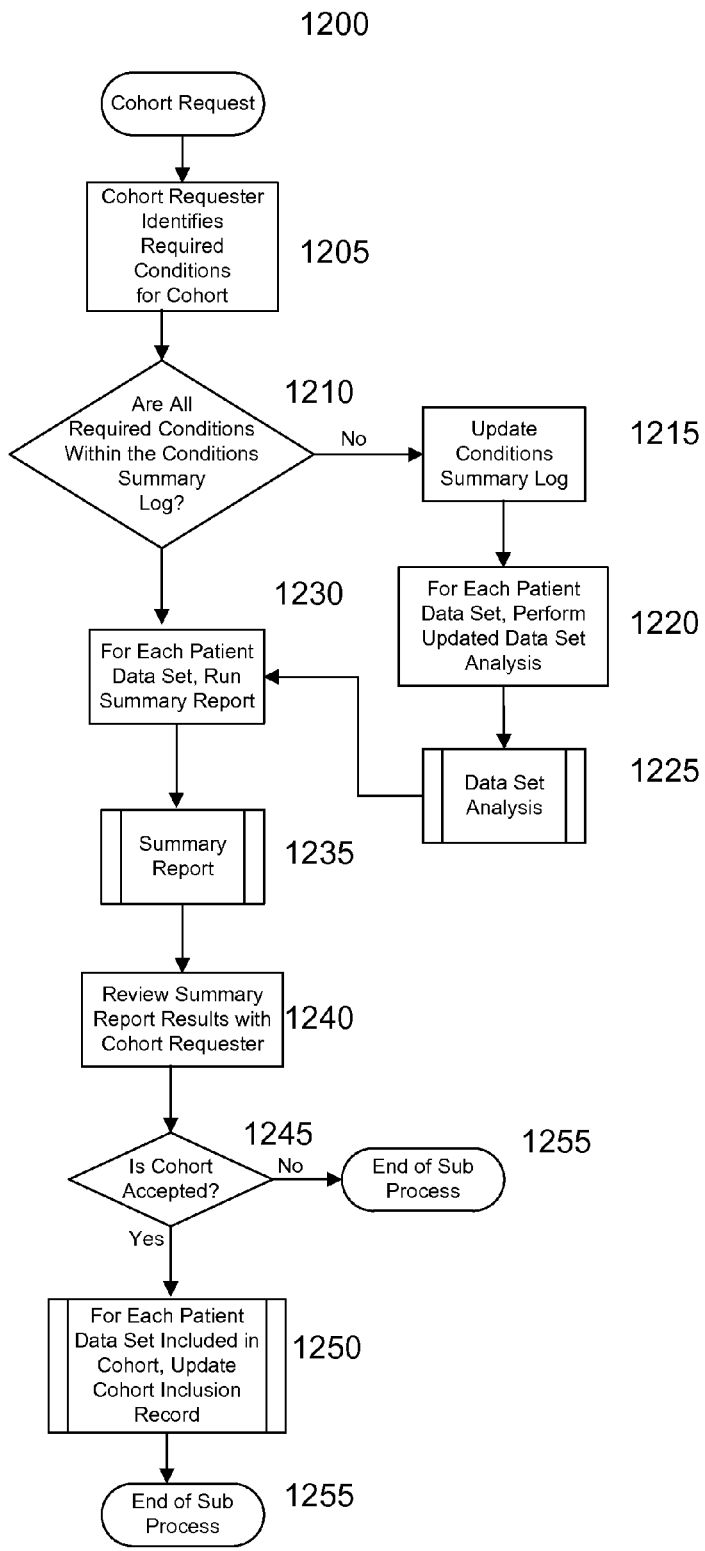
FIG. 12 depicts a cohort request process according to an embodiment of the invention.
Figure 13:
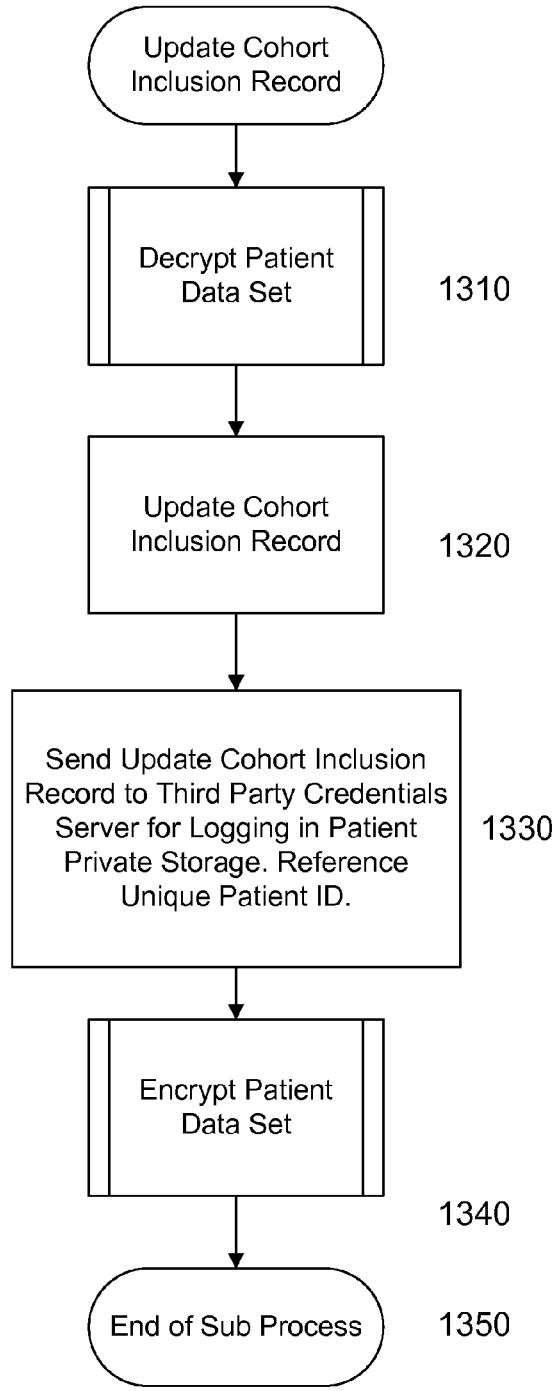
FIG. 13 depicts a cohort inclusion record update process according to an embodiment of the invention.

FIG. 12 depicts a cohort request process 1200 according to an embodiment of the invention. This process 1200 may be performed by one or more computers, for example the patient data set server 210, third party credentials server 220, third party key storage server 230, other computer 250, or some combination thereof. A cohort requester, such as a researcher or care provider, may identify conditions that define a cohort, and the system may receive these conditions 1205. A check may be performed to determine whether all specified conditions are conditions found within a conditions summary log 1210. The conditions summary log may be within the data store 10. If one or more specified conditions are not found, the conditions summary log may be updated 1215 to add the new condition or conditions. Then, for each patient data set in the data store 10, an updated data set analysis may be performed 1220. The data set analysis may be a process such as that described above with respect to FIG. 7, for example. Once the data set analysis is complete 1225, 700, a summary report may be run for each patient data set 1230. If all conditions were found within the conditions summary log, the summary report may be run for each patient data set 1230 without performing additional data set analysis. A summary report may be performed according to the process described below with respect to FIG. 14, for example. Once a summary report is run 1235, 1400, the summary report results may be presented to the cohort requester for review 1240. The system may receive data from the cohort requester indicating whether the summary report is accepted 1245. If the summary report is not accepted, the cohort request process 1200 may end. If the summary report is accepted, a cohort inclusion record associated with each patient data set included in the cohort may be updated 1250, 1300 as shown in FIG. 13, for example. Then the cohort request process 1200 may end 1260.

FIG. 13 depicts a cohort inclusion record update process 1250, 1300 according to an embodiment of the invention. This process 1250, 1300 may be performed by one or more computers, for example the patient data set server 210, third party credentials server 220, third party key storage server 230, other computer 250, or some combination thereof. First, a patient data set whose cohort inclusion record is to be updated may be decrypted 1310, 1000. Decryption may be done according to the process described above with respect to FIG. 10, for example. Once the data set is decrypted, its cohort inclusion record may be updated 1320 with information about the cohort to which it now belongs. The updated cohort inclusion record data may be sent to the third party credentials server 220 for logging in the associated patient private storage, which may be referenced using the unique patient ID 1330. The patient data set may be encrypted 1340, 1100, for example through the process described above with respect to FIG. 11. Encrypted patient data may be monetized in some embodiments. For example, patients can opt in for clinical trial opportunities once their data set is complete. The system may locate a patient cohort based on specifications input by the client. The specifications could be any combination of variables that the data core 10 holds. An operator of the data core 10 may either sell subscription access to commercial researchers or charge per patient referral. Any patient that completes a clinical trial may receive a share of what the operator receives. After encryption is complete, the cohort record update process 1250, 1300 may end 1350, and the cohort request process 1200 (or other process, if applicable) may continue as described above.

Figure 14:
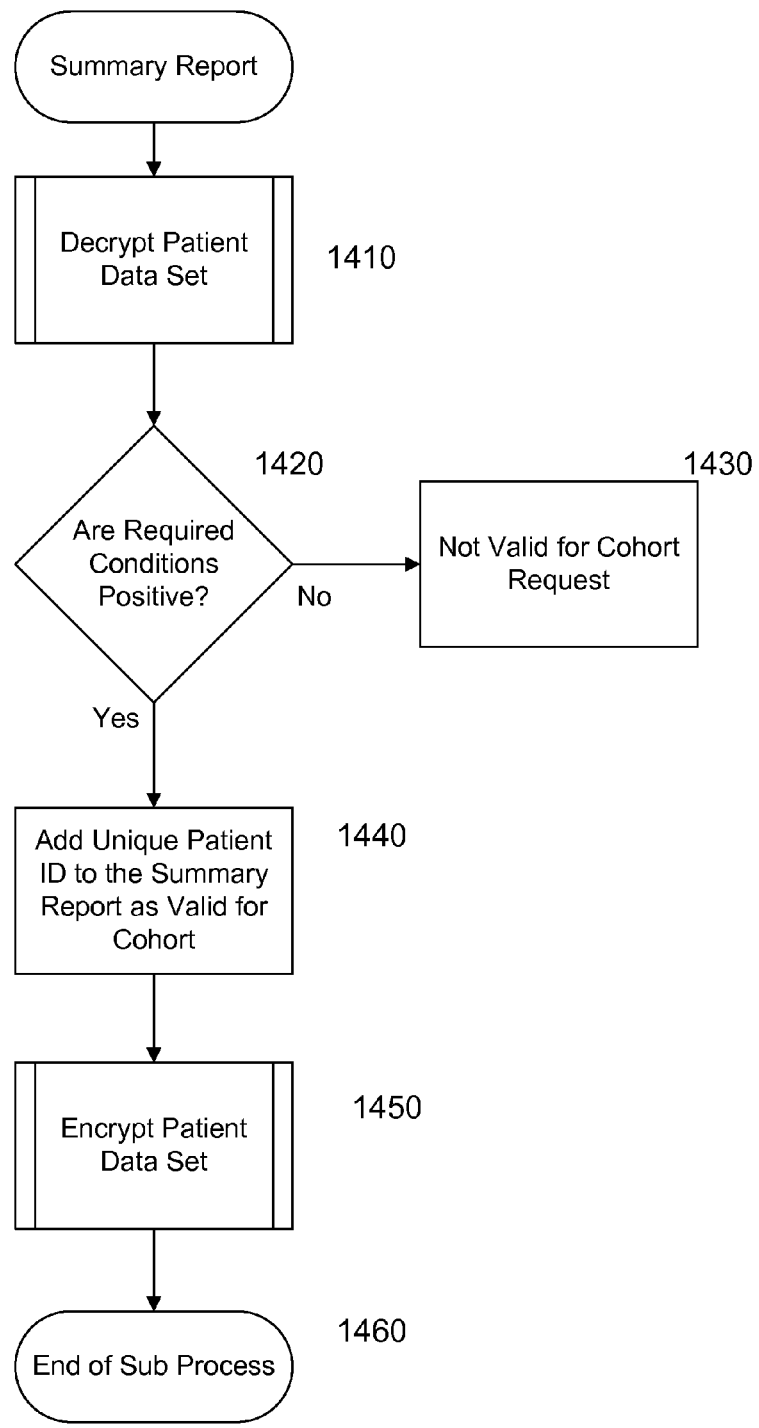
FIG. 14 depicts a summary report process according to an embodiment of the invention.

FIG. 14, depicts a summary report process 1235, 1400 according to an embodiment of the invention. This process 1235, 1400 may be performed by one or more computers, for example the patient data set server 210, third party credentials server 220, third party key storage server 230, other computer 250, or some combination thereof. First, a patient data set to be considered for addition to the summary report may be decrypted 1410, 1000, for example through the process described above with respect to FIG. 10. The decrypted patient data set may be analyzed to determine whether the conditions for inclusion in the cohort are met by the information in the patient data set 1420. If one or more of the conditions are not met, the patient data set may be deemed invalid for entry into the cohort that is the subject of the cohort request 1430. If the conditions are met, the unique patient ID associated with the patient data set may be added to the summary report for the cohort request, indicating that the patient data set may be valid for the cohort 1440. The patient data set may be encrypted 1450, 1100, for example through the process described above with respect to FIG. 11. After encryption is complete, the summary report process 1235, 1400 may end 1460, and the cohort request process 1200 (or other process, if applicable) may continue as described above.

Figure 15:
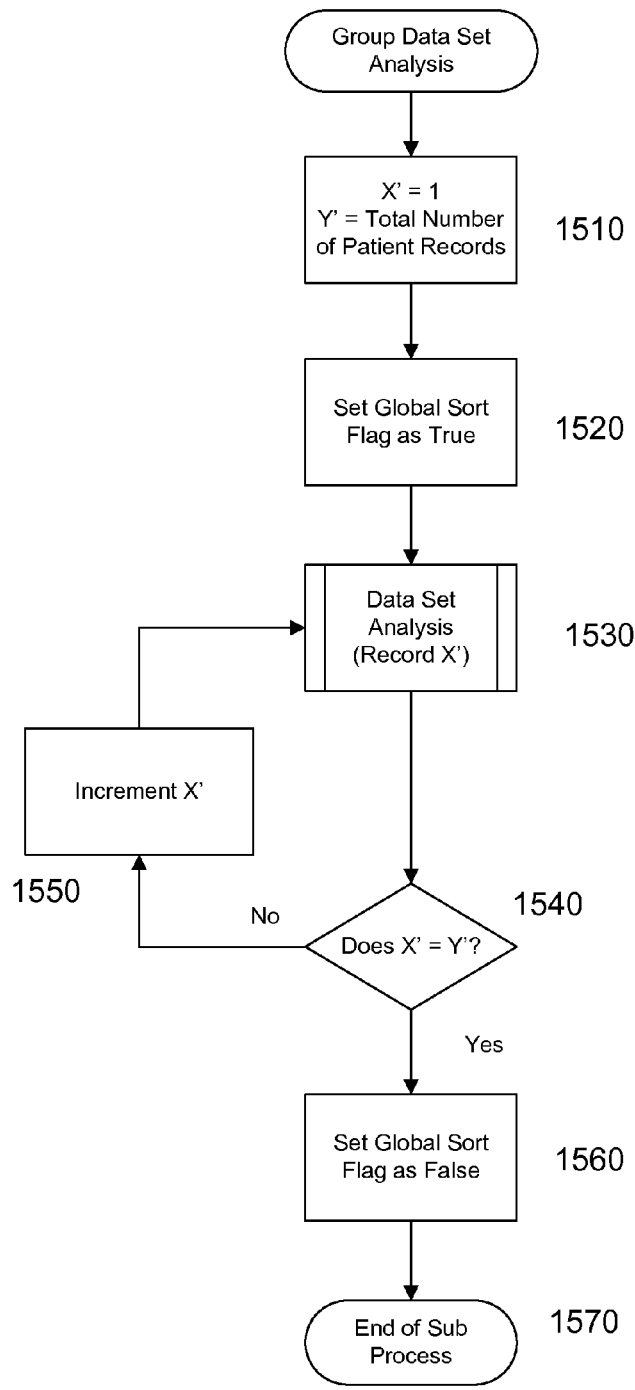
FIG. 15 depicts a group data set analysis process according to an embodiment of the invention.

FIG. 15 depicts a group data set analysis process 450, 1500 according to an embodiment of the invention. This process 450, 1500 may be performed by one or more computers, for example the patient data set server 210, third party credentials server 220, third party key storage server 230, other computer 250, or some combination thereof. When multiple patient data sets are to be analyzed, for example during analysis of an assembled cohort, the system may first set a variable $X'=1$ and a variable $Y'=$ a total number of patient records in the cohort 1510. A global sort flag may also be set as true 1520. Data set analysis may be performed on a record having an identifier equal to the value of $X'$ 1530, 700. For example, data set analysis may be performed according to the process described with respect to FIG. 7 above. After analysis of the data set corresponding to $X'$, the system may determine whether $X'=Y'$ 1540. If not, $X'$ may be incremented 1550, data set analysis may be performed on the data set corresponding to the new $X'$ 1530, and the new $X'$ may be compared to $Y'$

1540. When X'=Y', all patient records may have been analyzed, so the global sort flag may be set as false 1560 and the group data set analysis process 450, 1500 may end 1570. The patient data set development process 400 (or other process, if applicable) may continue as described above.

Figure 16:
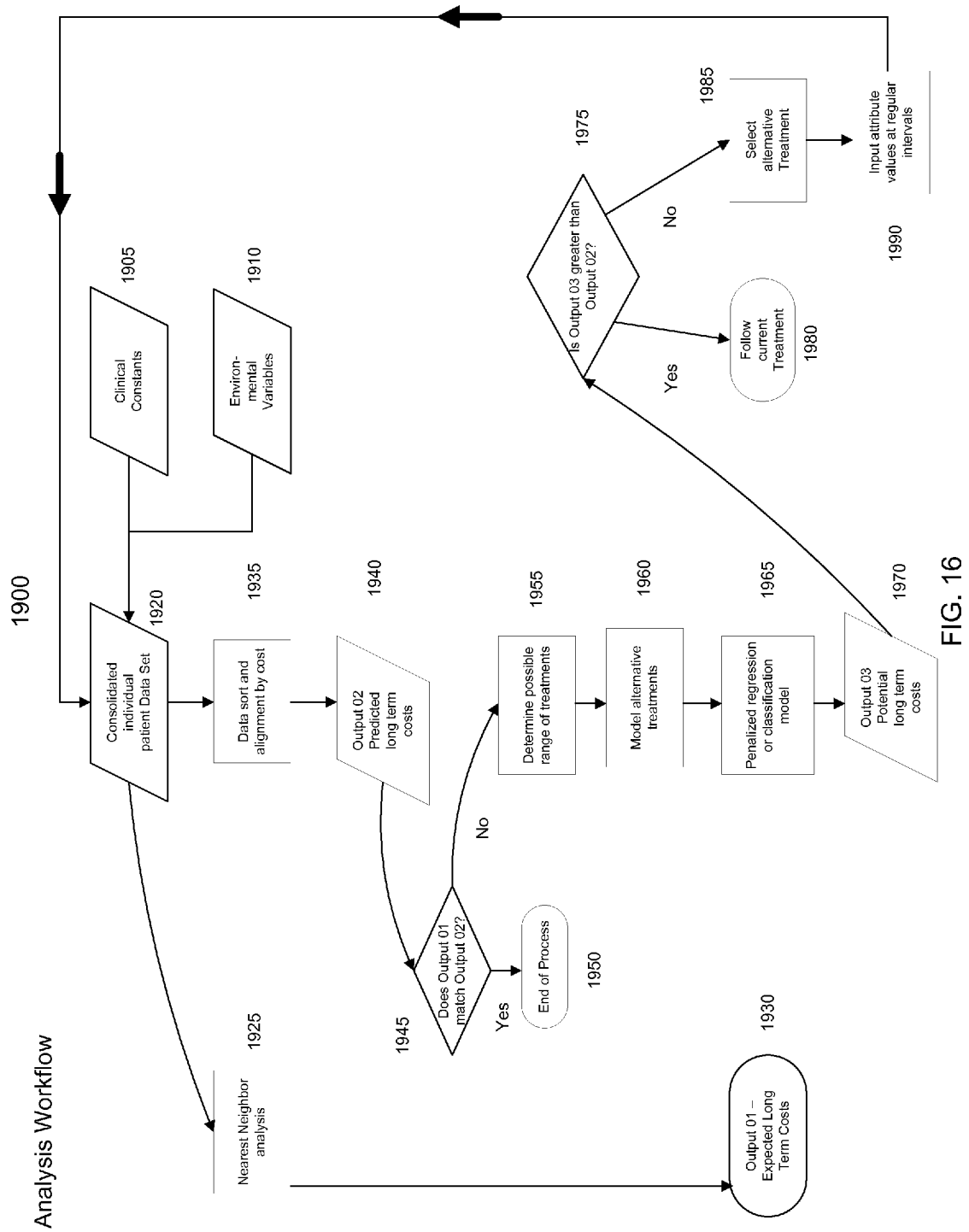
FIG. 16 depicts a workflow according to an embodiment of the invention.

FIGS. 4-15 detail the intake, de-identification, and operational processes that may be used to populate a user interface, the use and operation of which is described in FIG. 16. FIG. 16 depicts a workflow 1900 according to an embodiment of the invention. This process 1900 may express operations which may be used to see if a patient is having the CCO experience that their consolidated data set projects. This process 1900 may be employed by a patient, clinician, insurance company, and/or pharmaceutical company, for example. This process 1900 may be performed by one or more computers, for example the patient data set server 210, third party, credentials server 220, third party key storage server 230, other computer 250, or some combination thereof, to generate outputs which may be displayed to a user. Clinical constants 1905 and environmental variables 1910 such as those described above may be received and may be used to form a consolidated data set for an individual patient 1920. The clinical constants may represent the collection of observed disease specific attributes; this may be the patient's phenotypic state at inception into the core. Environmental variables could be geographic location, occupation, marital status, nutrition, etc. The consolidated data set may be the full patient profile combining the disease specific attributes and the environmental variables. A first algorithm performing a data sort and alignment by attribute, such as the nearest neighbor algorithm described with respect to FIG. 7 above, may be applied to the consolidated data set 1925, in which the patient's attributes may be used to search the data core 10 to find other patients with a similar set of attributes to analyze expected long term cost. The nearest neighbor algorithm may capture a real time view of the data core 10 and rank each patient by attribute similarity. The nearest neighbor algorithm may allow for the alignment of the patient into a category that may be expressed in a variety of ways, as described above. For example, patients may be grouped into deciles. Assuming that more disease attributes are worse than less disease attributes and that a patient has every attribute of a disease, it may be expected that the patient will appear in a first decile, which may indicate that 90% of the patients in the system have fewer attributes. The nearest neighbor algorithm may use the consolidated data set 1925 to produce a first output of predicted long term costs 1930 which may be displayed to a user. In the present example, the system may use the output of the nearest neighbor algorithm to place the patient in the appropriate decile category. Each decile may have a projected CCO value. Note that nearest neighbor data may be updated and enhanced every time a new patient's data is added to the data core 10, for example through the process described above with respect to FIG. 7. As more patient data sets enter the data core 10, more neighbors, and more similar neighbors, may become available. A second algorithm performing a data sort and alignment by cost, such as the penalized regression algorithm described above, may also be applied to the consolidated data set 1930 to produce a second output of predicted long term costs 1940 which may also be displayed to the user. The system may compare the first and second outputs 1945. If the outputs match or if the first output is less than the second output 1950, then the patient may be doing as well or poorly as expected, and this information may be displayed to a user 1930. If the outputs do not match 1950, a possible range of treatments may be determined 1955, and alternative treatments may be modeled 1960. Treatments may be finite for a given medical issue. For example, treatments may include, in order of cost/toxicity, cortico-steroids; mesalimine, (Asacol, Lialda) immune-suppresents, (Purenathol, Immuran,) biologics (Remicade, Humira, Tysabri, Cymzia), and/or a variety of surgical options. The penalized regression algorithm may sort the patient by CCOa (actual) as defined by cost for each treatment in this example. A treatment model may also be input or selected by a user. A third algorithm performing penalized regression or classification, such as the treatment-based cost algorithm described above, may be applied to the selected treatments 1965 to produce a third output of potential long term costs 1970 which may be displayed to a user. For example, if a patient falls into ninth decile on attributes and a first decile on costs, the treatment-based cost algorithm may allow for modeling of alternative clinical and therapeutic decisions that may have significant CCO impact. The treatment-based cost algorithm may include a penalized regression or classification model in order to forecast requested cost and complexity outcomes to a constituent group. For example, the penalized regression or classification model may incorporate the following data:

(A) Patient phenotype information (e.g. weight, height, presence or absence of a particular gene)
(B) Treatment history (e.g. treatment A followed by treatment B or treatment B followed by treatment A)
(C) All pairwise combinations of (A) and all combinations of (A) with (B)

Thus, the third and second outputs may be compared to determine which has a greater cost 1975. If the second output has a greater cost, the system may display a recommendation to follow the current treatment plan 1980. If the third output has a greater cost, the modeled alternative treatment information may be recommended and displayed 1985. As the alternative treatment progresses, data regarding the treatment may be input by a user at intervals 1990. This data may be incorporated into the consolidated individual patient data set. The patient/heuristic analysis workflow 1900 may be repeated as described above to incorporate the new data from the treatment. Outputs produced by this workflow 1900 may be displayed in the various interfaces described below with respect to FIGS. 17-21.

Figure 17:
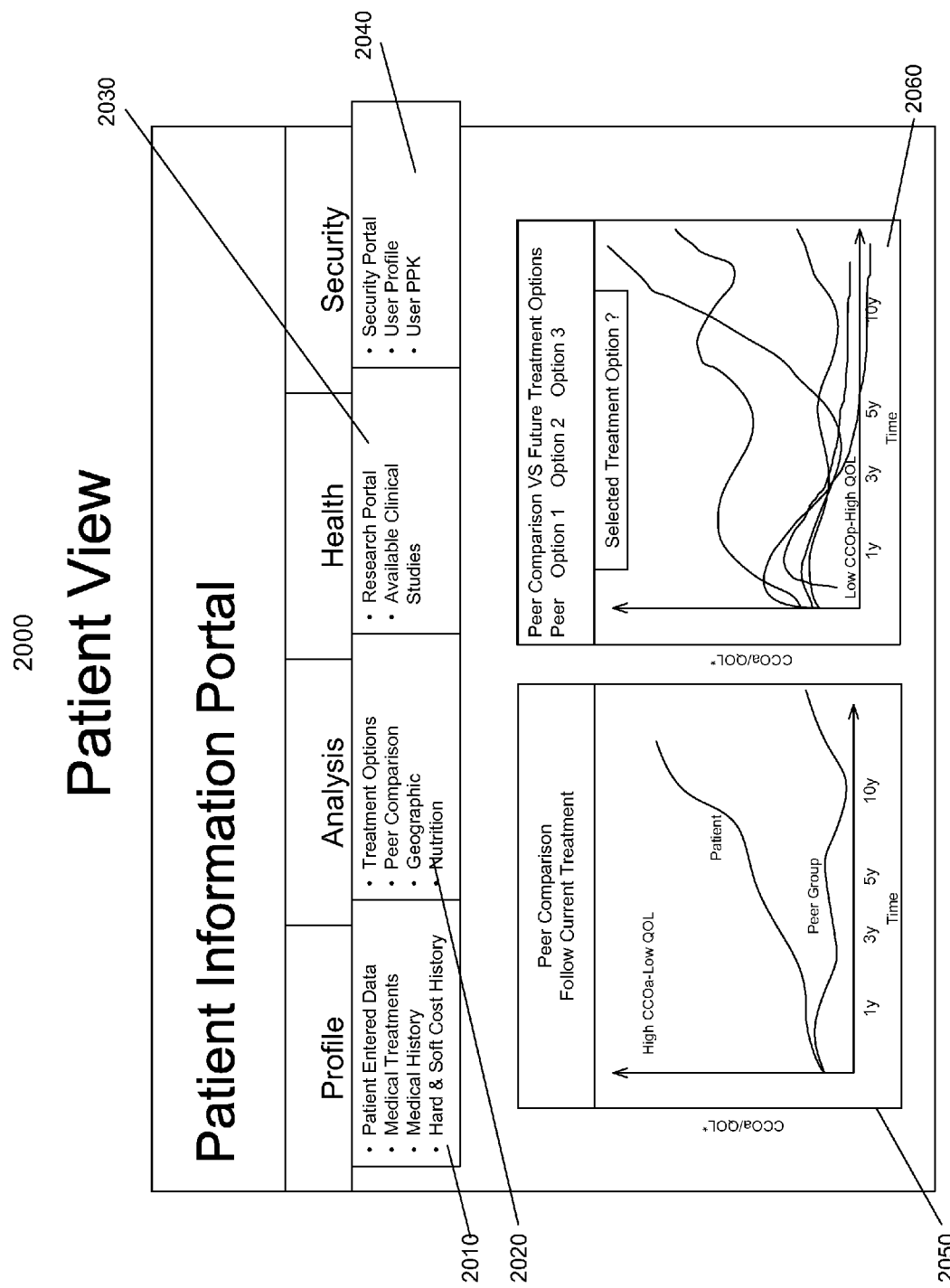
FIG. 17 depicts a patient view according to an embodiment of the invention.

FIG. 17 depicts a patient view 2000 according to an embodiment of the invention. This patient view 2000 is an example of a graphical user interface (GUI) which may be displayed to a user via a computer 250. The patient view 2000 may include a personal input form, which may enable a patient to enter data to be incorporated into a patient data set remotely, for example via a web browser. The patient view 2000 may include interactive elements such as a profile menu 2010, analysis menu 2020, health menu 2030, security menu 2040, and/or other interactive elements. The profile menu 2010 may enable a user to access patient entered data, medical treatment and medical history information for the patient, and/or cost history for the patient. The analysis menu 2020 may provide access to information on treatment options, patient to peer comparison data, and/or geographic or nutrition analysis data. The health menu 2030 may provide access to research portal information and available clinical studies in which the patient may participate. The security menu 2040 may provide access to a security portal, and may enable a user to access and/or modify a user profile and public/private key. The patient view 2000 may display data generated according to processes such as those described above. For example, the patient view 2000 may include a first output display 2050 of a peer comparison of a current treatment procedure and/or a second output display 2060 of a peer comparison of a possible future treatment option. The first output display 2050 may provide information that may forecast the patient's treatment compared to closely aligned cohorts, such as a graph of a patient projection for a cost/quality of life analysis over time compared to a peer group projection. The second output display 2060 may provide information that may forecast the patient's treatment compared to a more general population, such as a comparison of several treatment options on the same cost/quality of life over time scale. Furthermore, the information shown in the output displays 2050, 2060 may be selectable and/or dynamic. For example, different therapeutic choices may be selected and displayed, and the displays 2050, 2060 may update with new data entries into the relevant portions of the data core 10. Data shown in the first output display 2050 and second output display 2060 may be generated by, for example, the patient/heuristic analysis workflow 1900 as described above. Information presented in the patient view 2000 may enable a user to achieve . . .

1. Empowerment
2. Education around most practical course
3. Accessing other alternatives to therapy
4. Shared decision-making
5. Opportunity to participate in highly targeted trials and earn incentives.
6. Feel better—sooner and cheaper.

For example, 8 years ago, a 19 yr old female was diagnosed with Crohn's disease while in her sophomore year in college. Her GI followed evidence based guidelines and used corticosteroids to reduce activity and Asacol as a maintenance strategy. Multiple flares over the next 18 months resulted in hospitalizations and repeated Steroid dosing. Various immunosuppressant drugs were also tried and each proved ineffective. The GI was finally able to get the payer to authorize Remicade after demonstrating that there were no less costly options. Remicade did reduce the swelling, but accumulated damage to the young female had been done. An emergency Ileocecectomy was successfully performed followed by a week in the hospital. She has been well maintained on 6 mp immunosuppressant ever since. Her total cost thru hospital discharge was $220,000, and her total days absent from school was 22.

In the immediate future, another 19 year old female is diagnosed with Crohn's disease while away at school. Her GI inputs a pre-defined set of variables into a clinical practitioner computer 3 that moves the data into the data core 10. The patient's data may be aligned first by disease characteristics (attributes) of Crohn's disease and then by projected long term costs. Peer group comparison shows a projected high degree of cost and clinical encounters compared to other patients in the peer group. Previously established expert opinion has established that a certain genetic characteristic that is present in this patient indicates that the use of steroids at disease onset will cause her risk of surgery within 3 years to exceed an 85% probability. The GI successfully and confidently councils the patient and her family that a more aggressive course is called for. She is given 6 mp immuneosuppresent, and her disease activity is easily managed. Her total cost over an 18 month comparative period is $4000.

The patient has continuing access to her own real time personal health record and through a highly secure app on a patient computer 2. The patient may be asked to input information into the data core 10 via the patient computer 2 at pre-defined intervals. The app may allow the patient to ask heuristic questions that will produce answers specifically targeted to her particular phenotype, genetic characterization, and management of her gut bacteria. There may be no cost to the patient. The fact that the patient is sharing the treatment decision with the clinician and understands why and how the recommendation is being made has previously been proven to improve outcomes. The patient may also enroll in a clinical trial pool associated with the data core 10 and may be informed if and when an opportunity exists. The patient and data core 10 manager may share any revenue derived if the patient enrolls in and completes an appropriate study.

Figure 18:
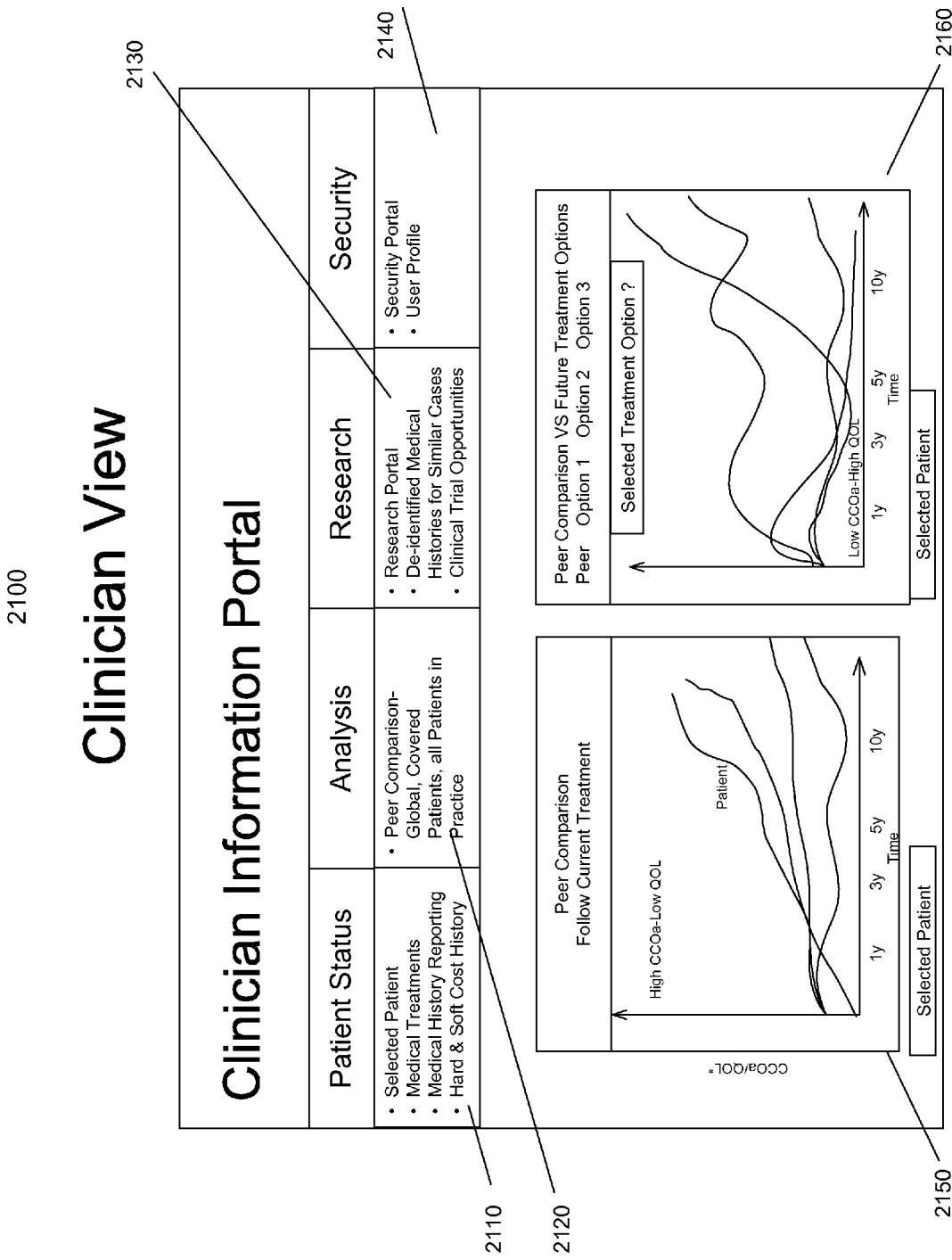
FIG. 18 depicts a clinician view according to an embodiment of the invention.

FIG. 18 depicts a clinician view 2100 according to an embodiment of the invention. This clinician view 2100 is an example of a GUI which may be displayed to a user via a computer 250. The clinician view 2100 may include interactive elements such as a patient status menu 2110, analysis menu 2120, research menu 2130, security menu 2140, and/or other interactive elements. The patient status menu 2110 may allow a user to access information shown in a patient view 2000 associated with a patient as described above, lists and/or information on some or all patients in a clinician's care, de-identified data on some or all patients in the clinician's care, in a particular hospital or accountable care organization (ACO), and/or in the data store 10. The patient status menu 2110 may enable a user to select patients, access medical treatment and medical history information for a patient, and/or cost history for the patient. The analysis menu 2120 may provide access to peer comparison data based on a variety of selection criteria such as global data, covered patient data, and/or patients in practice data. The research menu 2130 may provide access to research portal information, de-identified data for similar cases, and/or available clinical studies in which the patient may participate. The security menu 2140 may provide access to a security portal and may enable a user to access and/or modify a user profile. The clinician view 2100 may display data generated according to processes such as those described above. For example, the clinician view 2100 may include a first output display 2150 of a peer comparison of a current treatment procedure and/or a second output display 2160 of a peer comparison of a possible future treatment option. The first output display 2150 in this example illustrates a graph of a patient projection for a cost/quality of life analysis over time compared to several peer projections. The second output display 2160 in this example illustrates a graph of several treatment option projections for a cost/quality of life analysis over time for a patient. Data shown in the first output display 2150 and second output display 2160 may be generated by, for example, the analysis workflow 1900 as described above. Information presented in the clinician view 2100 may enable a user to . . .

1. Greater patient understanding; shared decision-making fosters better treatment compliance
2. Less lawsuits; possible lower malpractice premiums
3. Meets "meaningful use" of the ACA
4. Personal health record integrates with patient-entered updates
5. Evidence-based projections on complexity, cost and outcomes
6. Faster payer approvals For example, a clinician can empower the patient to join in the decision making for their individual treatment course by using the systems and methods described herein with the patient during an office visit. The clinician can also compare various treatments and patients to gain a better understanding of disease characteristics and treatment efficacies. Patient data sets may also be sortable by individual practitioner, which may allow a user to understand which practitioners have the most success treating specific diseases.

Figure 19:
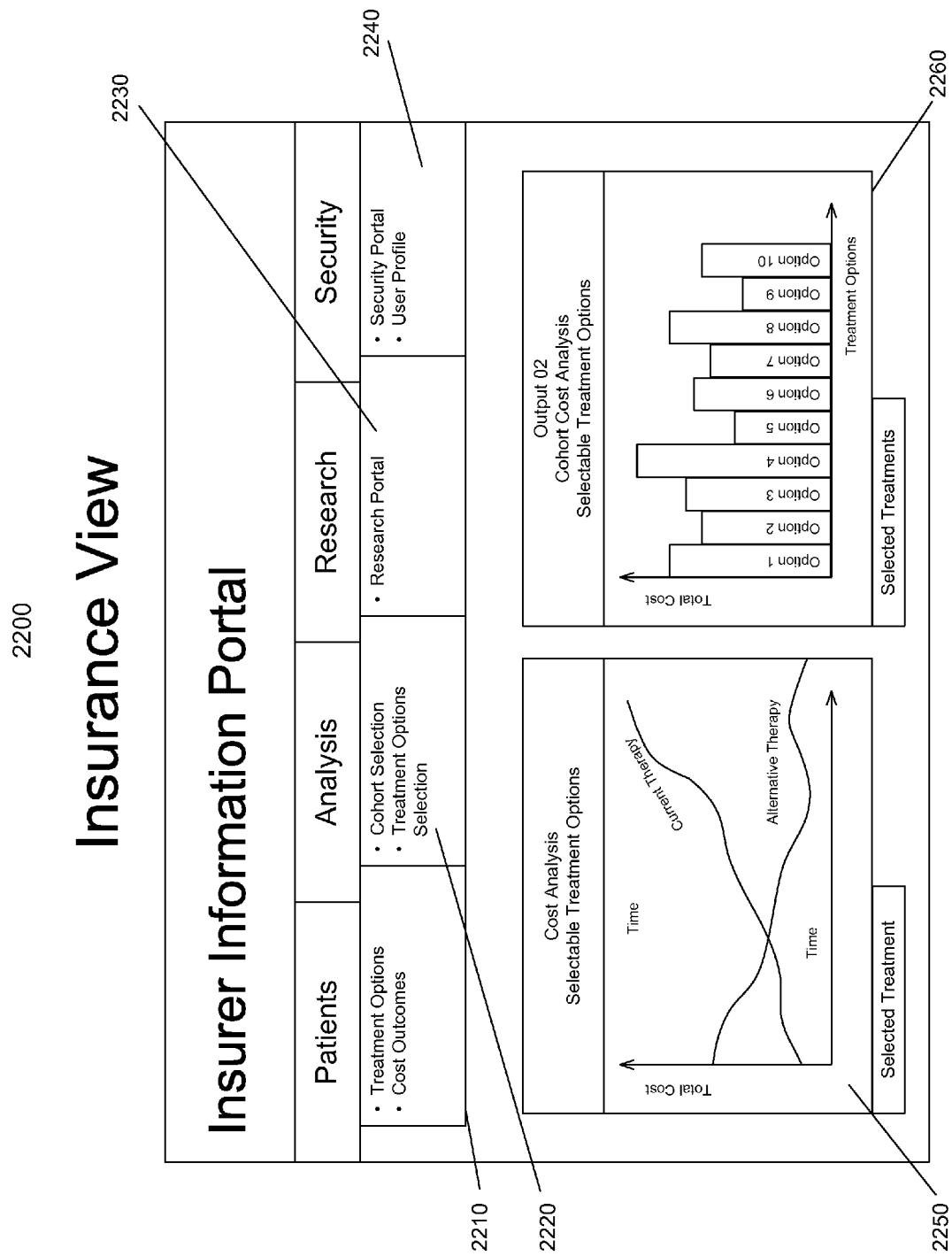
FIG. 19 depicts an insurance view according to an embodiment of the invention.

FIG. 19 depicts an insurance view 2200 according to an embodiment of the invention. This insurance view 2200 is an example of a GUI which may be displayed to a user via a computer 250. The insurance view 2200 may include interactive elements such as a patients menu 2210, analysis menu 2220, research menu 2230, security menu 2240, and/or other interactive elements. The patient menu 2210 may enable a user to select treatment options and/or cost outcomes for a patient. The analysis menu 2220 may provide access to cohort and treatment option data. The research menu 2230 may provide access to research portal information. The security menu 2240 may provide access to a security portal and may enable a user to access and/or modify a user profile. The insurance view 2200 may display data generated according to processes such as those described above. For example, the insurance view 2200 may include a first output display 2250 of a cost analysis of selectable treatment options and/or a second output display 2260 of a cohort cost analysis of selectable treatment options. Data shown in the first output display 2250 and second output display 2260 may be generated by, for example, the analysis workflow 1900 as described above. The insurance view 2200 may display data that may be of interest to entities such as health insurance companies, malpractice carriers, self-insured corporations, and the like. For example, the insurance view 2200 may display data such as real-time views of cost and complexity cohorts longitudinally entered and attached to patient records, immediate projections of the insured's cost and complexity wherein patient data may be aligned with closely matched cohort (as measured by attributes and patient-entered data), alerts highlighting individual records heading to higher cost/complexity levels, lowest long-term cost heuristic (what if) tools plotted in graphical crosshairs wherein each attribute may be solvable individually or in combination with other attributes/treatments, cost/complexity vs. patient complaints and lawsuits, physician users of the system described herein vs. nonusers, days missed from work due to illness, days missed from work to care for a patient, alerts to highlight employees heading to higher risk categories (with patient permission), and/or other information. Information presented in the insurance view 2200 may enable a user to . . .
1. Lower long-term cost
2. possible avoidance of unnecessary diagnostic procedures
3. Addresses most rapidly growing expenses of a disease-specific population
4. Lower administrative cost resulting from collaborative decisions based on data-generated recommendations
5. Lower cost through less frequent awards
6. Projections viewed collectively by patient and physician decreases litigation possibility
7. Lower, more competitive insurance rates offered to participating physicians/health care
8. Lower long-term insurance costs
9. Lower productivity losses due to employee absenteeism
10. Lower long-term disability costs For example, employers (who may be self-insured businesses) and/or insurance companies can see cost savings provided by different treatment options and see where cost improvements may be made. Employers may also be able to identify soft costs such as time missed from work due to illness and factor those costs into their decision making. Malpractice insurers may be able to make decisions based on the fact that a clinician using the systems and methods described herein can involve the patient in treatment decision making, as discussed above.

Figure 20:
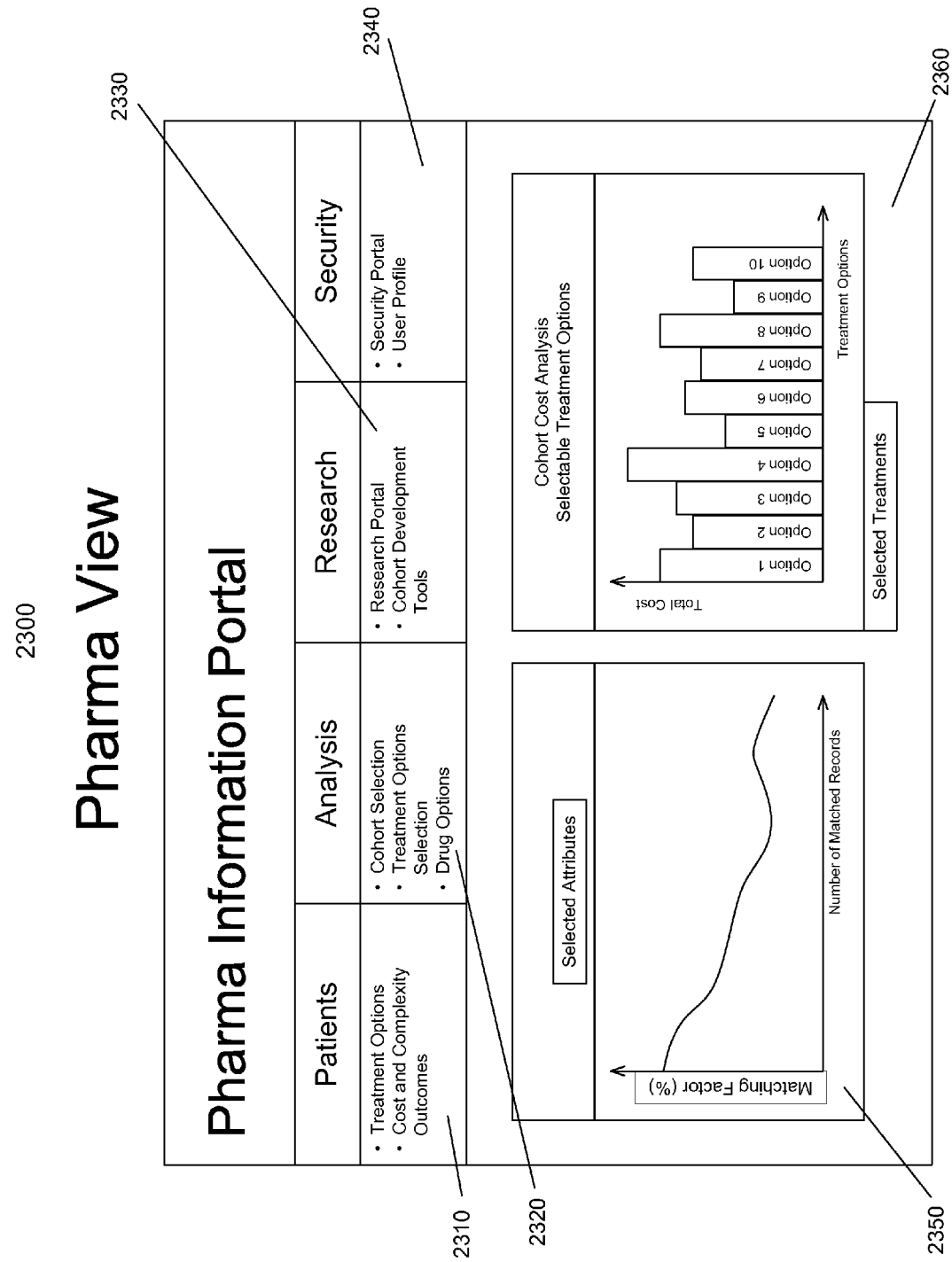
FIG. 20 depicts a Pharma view according to an embodiment of the invention.

FIG. 20 depicts a pharma view 2300 according to an embodiment of the invention. This pharma view 2300 is an example of a GUI which may be displayed to a user via a computer 250. The pharma view 2300 may include interactive elements such as a patients menu 2310, analysis menu 2320, research menu 2330, security menu 2340, and/or other interactive elements. The patient menu 2310 may enable a user to select treatment options and cost/complexity outcomes for a patient. The analysis menu 2320 may provide access to cohort, treatment option, and/or drug option selection data. The research menu 2330 may provide access to research portal information and/or cohort development tools enabling a user to define a cohort. The security menu 2340 may provide access to a security portal and may enable a user to access and/or modify a user profile. The pharma view 2300 may display data generated according to processes such as those described above. For example, the pharma view 2300 may include a first output display 2350 of a cost analysis of selectable treatment options and/or a second output display 2360 of a cohort cost analysis of selectable treatment options. Data shown in the first output display 2350 and second output display 2360 may be generated by, for example, the analysis workflow 1900 as described above. For example, pharma view 2300 may display data such as a current view of cost and complexity cohorts longitudinally entered and attached to patient records, a lowest long-term cost heuristic (what if) display plotted in graphical crosshairs wherein each attribute may be solvable individually or in combination with other attributes/treatments, a display solving for any drug in the database versus patient attributes and outcomes as well as in combination with other therapies, a custom input screen allowing for targeted searches at the individual data point level to develop candidates for clinical trials, and/or other information. Information presented in the pharma view 2300 may enable a user to . . .
1. Real-time view of market penetration of underlying drug solved geographically, phenotypically, environmentally.
2. On demand analysis of drugs therapeutic value when given in combination with other therapies.
3. Rapid cohort identification for the purpose of enrolling late stage clinical trials.
4. Early identification of a particular drugs concordance or discordance with other therapies.
5. Identify geographic areas where supplemental education would prove useful.

For example, pharmaceutical companies may enter information about upcoming clinical trials into the system, and clinicians may be able to view this information and advise clients who may be eligible for trials of the opportunities to opt in. Pharmaceutical companies themselves may also be able to analyze the data in the data core 10 to identify patient data sets of interest, and may contact the clinicians associated with the identified patient data sets. As discussed above, patient data sets may be de-identified so that pharmaceutical users are not aware of a patient's identity until after they opt in to a clinical trial. Clinicians may be given incentives to help register clients, and clients may be paid for joining trials. Pharmaceutical companies may therefore be able to easily build a pool of trial patients, because the systems and methods described herein may be able to sort patients according to the attributes that are desirable for clinical study.

Figure 21:
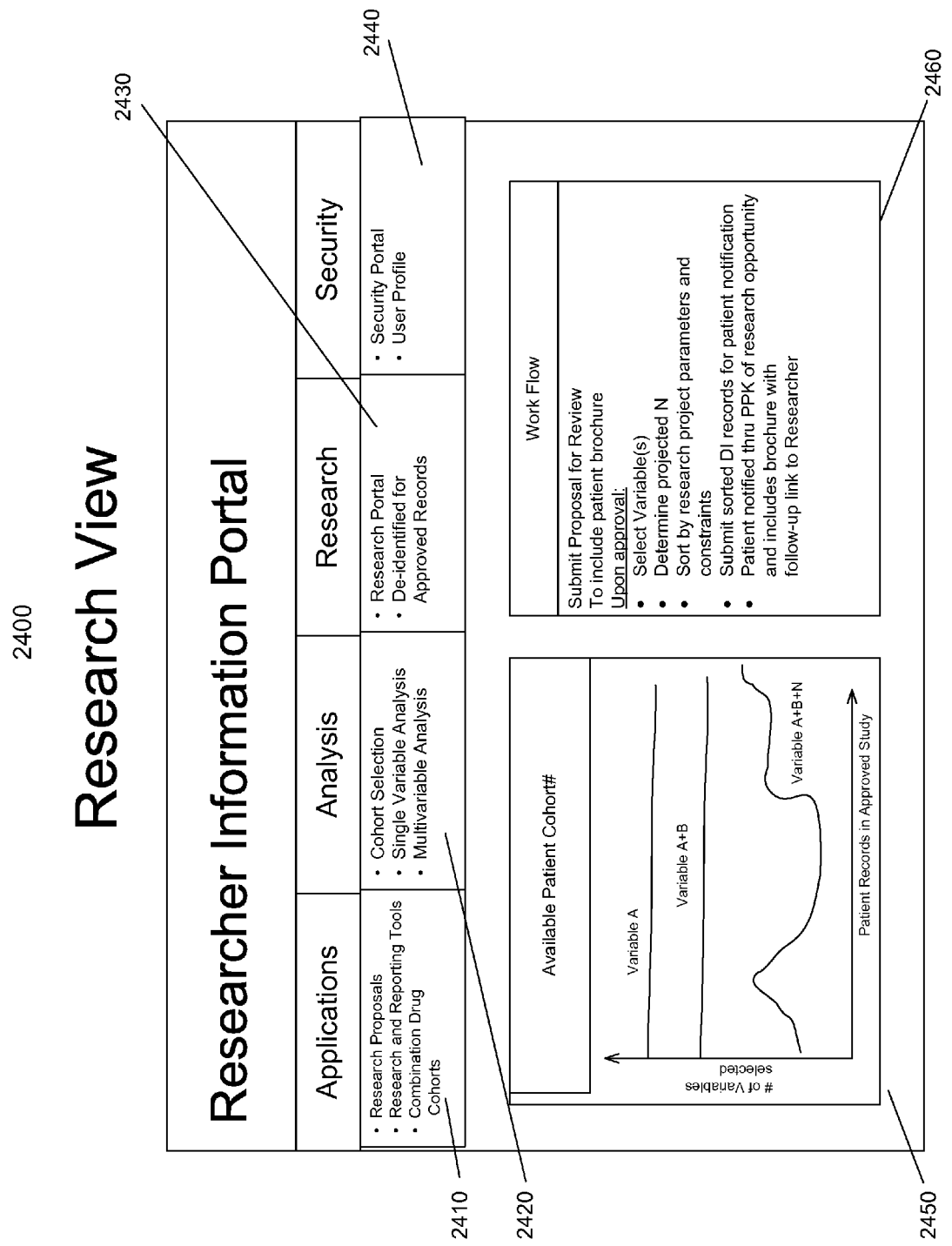
FIG. 21 depicts a research view according to an embodiment of the invention.

FIG. 21 depicts a research view 2400 according to an embodiment of the invention. This research view 2400 is an example of a GUI which may be displayed to a user via a computer 250. The research view 2400 may include interactive elements such as an applications menu 2410, analysis menu 2420, research menu 2430, security menu 2440, and/or other interactive elements. The applications menu 2410 may enable a user to select research proposals, research reporting tools, and/or combination drug cohort data. The analysis menu 2420 may provide cohort selections and single and/or multi variable analysis tools. The research menu 2430 may provide access to research portal information and/or de-identified patient data. The security menu 2440 may provide access to a security portal and may enable a user to access and/or modify a user profile. The research view 2400 may display data generated according to processes such as those described above. For example, the research view 2400 may include a first output display 2450 of available patients for a cohort graphed as a number of available patient records vs. a number of selected variables and/or a second output display 2460 of a proposal workflow. Data shown in the first output display 2450 and second output display 2460 may be generated by, for example, the patient/heuristic analysis workflow 1900 as described above. The research view 2400 may display data that may be of interest to entities such as basic researchers, nonprofits such as health care charities or academic institutions, those identifying translational opportunities, and the like. For example, the research view 2400 may provide information such as access to basic analysis tools with multivariable analysis, access to sorting tools which may be customized to correspond to a research proposal, and/or unrestricted views of the de-identified global data set. In some cases, the level of access to this information may be based upon approval of a research proposal and/or the scope of the research proposal. Access may also be based upon research request submissions, shared or joint IP agreements, or previously licensed access. Additionally, real-time views of a current state and progression of a disease, epidemiological views, environmental views, patient and/or physician entered data, and/or potential translational opportunities may be accessible. Information presented in the research view 2400 may enable a user to . . .

1. Real-time view of disease trends, prevalence and incidence
2. ability to test outside research against real-world data
3. possibility of collaborating in pursuing translational opportunities with shared intellectual property rights.
4. Access to highly discreet cohorts without the time or expense, of assembling study subjects
5. ability to solicit patient participation through the public-private key based on specific disease attribute requests.
6. percentage of patients as members of underlying nonprofit institution or support groups
7. ability to request D I patients opt in to either membership or email
8. cohort identification tool to identify likely study candidates—(DI)
9. options to fund and/or administer targeted research
10. possibility of identifying new disease markers
11. possibility of identifying novel genetic pathways to target for new therapies
12. ability to provide research subjects to test "orphan drugs"

For example, a researcher may be able to observe new patient data sets as they are entered and identify patterns in treatments applied to given sets of attributes. This may allow a researcher to identify areas of potentially interesting research, for example by enabling identification of extant problems which might otherwise have been difficult to see by examining unsorted sets of patient data.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. For example, while the above examples are presented in the context of OPSs 200 connecting to nodes 150, it will be understood that the systems and methods described herein can be performed by any interconnected computers. Thus, the present embodiments should not be limited by any of the above-described embodiments.

In addition, it should be understood that any figures which highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

What is claimed is:

1. A method comprising:
    grouping, with a processor in communication with a database, a plurality of de-identified data sets into a plurality of cohorts, each of the plurality of de-identified data sets being derived from data associated with one of a plurality of patients and each of the plurality of de-identified data sets comprising at least one attribute, each cohort comprising at least one of the plurality of de-identified data sets grouped together based on at least one similarity of the at least one attribute;
    receiving, with the processor, a patient data set comprising at least one of the attributes, the patient data set associated with a patient having a treatable medical condition or disease;
    determining, with the processor, a relationship between the patient data set and one of the plurality of cohorts based on a similarity between the at least one attribute of the patient data set and the at least one attribute of the cohort;
    determining, with the processor, a predicted treatment cost associated with the one of the plurality of cohorts;
    receiving, with the processor, an evidence-based treatment cost for the patient, the evidence-based treatment cost being the cost of an evidence-based treatment for the treatable medical condition or disease;
    comparing, with the processor, the evidence-based treatment cost to the predicted treatment cost;
    when the evidence-based treatment cost is greater than the predicted treatment cost, generating, with the processor, an alternative treatment for the treatable medical condition or disease based on the one of the plurality of cohorts, the alternative treatment being different from the evidence-based treatment;
    determining, with the processor, an alternative predicted treatment cost associated with the alternative treatment;
    comparing, with the processor, the evidence-based treatment cost to the alternative predicted treatment cost;
    generating, with the processor, a treatment recommendation based on the comparing of the evidence-based treatment cost to the alternative predicted treatment cost;
    de-identifying, with the processor, the patient data set to generate a new de-identified data set that is not associated with the patient;
    encrypting, with the processor, the new de-identified data set to generate an encrypted data set; and
    storing, with the processor, the encrypted data set in the database as one of the plurality of de-identified data sets.

2. The method of claim 1, further comprising:
    generating, with the processor, a patient account for the patient.

3. The method of claim 2, wherein the generating of the patient account comprises:
   generating, with the processor, a unique patient ID;
   receiving, with the processor, a public de-identification key;
   storing, with the processor, the public de-identification key and the unique patient ID in the database;
   receiving, with the processor, a public data set encryption key;
   encrypting, with the processor, the unique patient ID with the public data set encryption key to generate an encrypted ID; and
   storing, with the processor, the encrypted ID in the database.

4. The method of claim 3, further comprising:
   retrieving, with the processor, the public de-identification key from the database;
   encrypting, with the processor, data within the patient data set that identifies an identity of the patient; and
   inserting, with the processor, the encrypted ID into the patient data set.

5. The method of claim 3, further comprising:
   analyzing, with the processor, a log file associated with the patient data set to determine whether it matches an expected state;
   generating, with the processor, a public data set encryption key and a private data set encryption key;
   updating, with the processor, the log file; and
   encrypting, with the processor, the unique patient ID, the log file, and the patient data set.

6. The method of claim 1, wherein the patient data set comprises:
   a biographical record associated with the patient, a patient record associated with the patient, a treatment record associated with the patient, or a combination thereof.

7. The method of claim 1, wherein grouping the plurality of de-identified data sets into the plurality of cohorts comprises:
   receiving, with the processor, a definition of a cohort;
   associating, with the processor, each of the plurality of de-identified data sets that complies with the definition of the cohort with the cohort so that the cohort comprises at least one of the plurality of de-identified data sets; and
   analyzing, with the processor, the cohort to generate a cohort data set analysis.

8. The method of claim 1, further comprising:
   decrypting, with the processor, the encrypted data set to generate a decrypted data set;
   classifying, with the processor, an attribute of the decrypted data set and/or the new de-identified data set;
   analyzing, with the processor, the attribute of the decrypted data set and/or the new de-identified data set;
   encrypting, with the processor, the decrypted data set and/or the new de-identified data set; and
   purging, with the processor, unencrypted data associated with the decrypted data set and/or the new de-identified data set.

9. The method of claim 1, further comprising:
   determining, with the processor, whether a global sort flag is set; and
   incorporating, with the processor, the predicted treatment cost into a report when the global sort flag is set.

10. The method of claim 1, wherein the determining of the alternative predicted treatment cost comprises:
    receiving, with the processor, a treatment cost associated with the alternative treatment from the database;
    adding, with the processor, the treatment cost to a total cost associated with the attribute;
    storing, with the processor, the total cost in the database;
    dividing, with the processor, the total cost by a treatment period associated with the treatment to generate the alternative predicted treatment cost; and
    storing, with the processor, the alternative predicted treatment cost in the database.

11. The method of claim 1, wherein the determining of the predicted treatment cost comprises:
    receiving, with the processor, a cost associated with the one of the plurality of cohorts; and
    predicting, with the processor, the predicted cost based on the cost associated with the one of the plurality of cohorts.

12. The method of claim 1, wherein determining the relationship comprises performing a nearest neighbor analysis on the patient data set and the plurality of cohorts.

13. The method of claim 1, wherein the determining of the predicted treatment cost and the determining of the alternative predicted treatment cost comprise performing a penalized regression analysis.

14. The method of claim 1, further comprising causing, with the processor, a display to display the determined relationship, the predicted treatment cost, the alternative predicted treatment cost, the treatment recommendation, or a combination thereof.

15. The method of claim 7, wherein grouping the plurality of de-identified data sets into the plurality of cohorts further comprises, for each of the plurality of de-identified data sets:
    identifying, with the processor, a condition associated with the cohort in the request for analysis of the cohort;
    generating, with the processor, a summary report for the de-identified data set;
    reporting, with the processor, the summary report;
    receiving, with the processor, an acceptance of the de-identified data set; and
    incorporating, with the processor, the de-identified data set into the cohort.

16. The method of claim 15, wherein the generating of the summary report for each of the plurality of de-identified data sets comprises, for each of the plurality of de-identified data sets:
    decrypting, with the processor, the de-identified data set to generate a decrypted data set;
    analyzing, with the processor, the decrypted data set to determine whether the decrypted data set satisfies the condition;
    generating, with the processor, a record indicating that the unique patient ID associated with the encrypted data set is valid for the cohort; and
    encrypting, with the processor, the decrypted data set.

17. A system comprising:
    a database; and
    a processor in communication with the database, the processor being constructed and arranged to:
    group a plurality of de-identified data sets into a plurality of cohorts, each of the plurality of de-identified data sets being derived from data associated with one of a plurality of patients and each of the plurality of de-identified data sets comprising at least one attribute, each cohort comprising at least one of the plurality of de-identified data sets grouped together based on at least one similarity of the at least one attribute;
    receive a patient data set comprising at least one of the attributes, the patient data set associated with a patient having a treatable medical condition or disease;
    determine a relationship between the patient data set and one of the plurality of cohorts based on a similarity between the at least one attribute of the patient data set and the at least one attribute of the cohort;
determine a predicted treatment cost associated with the one of the plurality of cohorts;
receive an evidence-based treatment cost for the patient, the evidence-based treatment cost being the cost of an evidence-based treatment for the treatable medical condition or disease;
compare the evidence-based treatment cost to the predicted treatment cost;
when the evidence-based treatment cost is greater than the predicted treatment cost, generate an alternative treatment for the treatable medical condition or disease based on the one of the plurality of cohorts, the alternative treatment being different from the evidence-based treatment;
determine an alternative predicted treatment cost associated with the alternative treatment;
compare the evidence-based treatment cost to the alternative predicted treatment cost;
generate a treatment recommendation based on the comparing of the evidence-based treatment cost to the alternative predicted treatment cost;
de-identify the patient data set to generate a new de-identified data set that is not associated with the patient;
encrypt the new de-identified data set to generate an encrypted data set; and
store the encrypted data set in the database as one of the plurality of de-identified data sets.

18. The system of claim 17, wherein the processor is further constructed and arranged to generate a patient account for the patient.

19. The system of claim 18, wherein the processor is constructed and arranged to generate the patient account by:
generating a unique patient ID;
receiving a public de-identification key;
storing the public de-identification key and the unique patient ID in the database;
receiving a public data set encryption key;
encrypting the unique patient ID with the public data set encryption key to generate an encrypted ID; and
storing the encrypted ID in the database.

20. The system of claim 19, wherein the processor is further constructed and arranged to:
retrieve the public de-identification key from the database;
encrypt data within the patient data set that identifies an identity of the patient; and
insert the encrypted ID into the patient data set.

21. The system of claim 19, wherein the processor is further constructed and arranged to:
analyze a log file associated with the patient data set to determine whether it matches an expected state;
generate a public data set encryption key and a private data set encryption key;
update the log file; and
encrypt the unique patient ID, the log file, and the patient data set.

22. The system of claim 17, wherein the patient data set comprises:
a biographical record associated with the patient, a patient record associated with the patient, a treatment record associated with the patient, or a combination thereof.

23. The system of claim 17, wherein the processor is constructed and arranged to group the plurality of de-identified data sets into the plurality of cohorts by:
receiving a definition of a cohort;
associating each of the plurality of de-identified data sets that complies with the definition of the cohort with the cohort so that the cohort comprises at least one of the plurality of de-identified data sets; and
analyzing analyze the cohort to generate a cohort data set analysis.

24. The system of claim 17, wherein the processor is further constructed and arranged to:
decrypt the encrypted data set to generate a decrypted data set;
classify an attribute of the decrypted data set and/or the new de-identified data set;
analyze the attribute of the decrypted data set and/or the new de-identified data set;
encrypt the decrypted data set and/or the new de-identified data set; and
purge unencrypted data associated with the decrypted data set and/or the new de-identified data set.

25. The system of claim 17, wherein the processor is further constructed and arranged to:
determine whether a global sort flag is set; and
incorporate the predicted treatment cost into a report when the global sort flag is set.

26. The system of claim 17, wherein the processor is constructed and arranged to determine the alternative predicted treatment cost by:
receiving a treatment cost associated with the alternative treatment from the database;
adding the treatment cost to a total cost associated with the attribute;
storing the total cost in the database;
dividing the total cost by a treatment period associated with the treatment to generate the alternative predicted treatment cost; and
storing the alternative predicted treatment cost in the database.

27. The system of claim 17, wherein the processor is constructed and arranged to determine the predicted treatment cost by:
receiving a cost associated with the one of the plurality of cohorts; and
predicting the predicted cost based on the cost associated with the one of the plurality of cohorts.

28. The system of claim 17, wherein the processor is constructed and arranged to determine the relationship by performing a nearest neighbor analysis on the patient data set and the plurality of cohorts.

29. The system of claim 17, wherein the processor is constructed and arranged to determine the predicted treatment cost and determine the alternative predicted treatment cost by performing a penalized regression analysis.

30. The system of claim 17, wherein the processor is further constructed and arranged to cause a display to display the determined relationship, the predicted treatment cost, the alternative predicted treatment cost, the treatment recommendation, or a combination thereof.

31. The system of claim 23, wherein the processor is constructed and arranged to group the plurality of de-identified data sets into the plurality of cohorts by, for each of the plurality of de-identified data sets:
identifying a condition associated with the cohort in the request for analysis of the cohort;
generating a summary report for the de-identified data set;
reporting the summary report;
receiving an acceptance of the de-identified data set; and
incorporating the de-identified data set into the cohort.

32. The system of claim 31, wherein the processor is constructed and arranged to generate the summary report for each of the plurality of de-identified data sets by, for each of the plurality of de-identified data sets:
- decrypting the de-identified data set to generate a decrypted data set;
- analyzing the decrypted data set to determine whether the decrypted data set satisfies the condition;
- generating a record indicating that the unique patient ID associated with the encrypted data set is valid for the cohort; and
- encrypting the decrypted data set.

* * * * *